United States Patent [19]

Lambeir et al.

[11] Patent Number: 5,384,257
[45] Date of Patent: * Jan. 24, 1995

[54] GLUCOSE ISOMERASES WITH AN ALTERED PH OPTIMUM

[75] Inventors: Anne-Marie Lambeir, Heverlee; Ignace Lasters, Antwerp; Nadir Mrabet, Hoeilaart, all of Belgium; Wilhelmus J. Quax, Voorschoten, Netherlands; Jan M. Van der Laan, Groningen, Netherlands; Onno Misset, Delft, Netherlands

[73] Assignees: Gist-brocades, N.V., Delft, Netherlands; Plant Genetics System, NV, Brussels, Belgium

[*] Notice: The portion of the term of this patent subsequent to May 10, 2011 has been disclaimed.

[21] Appl. No.: 112,703

[22] Filed: Aug. 26, 1993

Related U.S. Application Data

[63] Continuation of Ser. No. 637,399, Jan. 4, 1991.

[30] Foreign Application Priority Data

Jan. 4, 1990 [EP] European Pat. Off. ........... 90200030
Jan. 4, 1990 [EP] European Pat. Off. ........... 90200037

[51] Int. Cl.$^6$ ............... C12N 13/61; C12N 9/92; C12N 15/70; C12N 15/74
[52] U.S. Cl. ............................. 435/234; 435/69.1; 435/172.3; 435/252; 435/3.257.33; 536/23.2; 935/10; 935/14; 935/60; 935/72; 935/75
[58] Field of Search ............... 435/234, 69.1, 172.3, 435/252.3, 252.33, 320.1, 23.2

[56] References Cited

U.S. PATENT DOCUMENTS 4,609,625 9/1986 Keyes et al. ............... 435/176
4,894,331 6/1990 Ratzkin et al. ............... 435/94
5,041,378 8/1991 Drummond et al. ............... 435/234

FOREIGN PATENT DOCUMENTS 90-0196 1/1990 WIPO ............... 435/234

OTHER PUBLICATIONS

Collyer, C. A., et al., Mar. 1990, Journal of Molecular Biology, 212(1): 211-235.
Henrik, K., et al., 1989, Journal of Molecular Biology, 208(1): 129-157.
Batt, C. A., et al., Jan. 1990, Proceedings of the National Academy of Sciences, U.S.A., 87: 618-622.
Carrell, H. L., et al., 1989, Proceedings of the National Academy of Sciences, U.S.A., 86: 4440-4444.
Amore, R., et al., 1989, Nucleic Acids Research, 17(18): 7515.
Procourt, P., et al., 1988 Nucleic Acids Research, 16(19): 9337.
Muraki, M., et al., 1988, Protein Engineering, 2(1): 49-54.
Zvelebil, M. J. J. M., et al., 1988, Protein Engineering, 2(2): 127-138.
Farber, G. K., et al., 1988, Proceedings of the National Academy of Sciences, U.S.A., 85: 112-115.
Farber, G. K., et al., 1987, Protein Engineering, 1:467-469.

(List continued on next page.)

Primary Examiner—Robert A. Wax
Assistant Examiner—William W. Moore
Attorney, Agent, or Firm—Morrison & Foerster

[57] ABSTRACT

A method for selecting amino acid residues is disclosed which upon replacement will give rise to an enzyme with an altered pH optimum. The method is specific for metalloenzymes which are inactivated at low pH due to the dissociation of the metal ions. The method is based on altering the $pK_a$ of the metal coordinating ligands or altering the $K_{ass}$ for the metal binding. New glucose isomerases with an altered pH optimum are provided according to this method. These altered properties enable starch degradation to be performed at lower pH values.

15 Claims, 13 Drawing Sheets

FOREIGN PATENT DOCUMENTS

Henrik, K., et al., 1987, Protein Engineering, 1:459–460.

Saari, G. C., et al., 1987, Journal of Bacteriology, 169(2):612–618.

Sternberg, M. J. E., et al., 1987, Nature, 330:86–88.

Wells, J. A., et al., 1987, Proceedings of the National Academy of Sciences, U.S.A., 84:1219–1223.

Russel, A. J., et al., 1987, Journal of Molecular Biology 193:803–813.

Thomas, P. G., et al., 1987, Nature, 318:375–376.

Chen, "Glucose Isomerase (a Review)", Process Biochemistry, pp. 30–35 (Jun./Jul. 1980).

Chen, "Glucose Isomerase (a Review)", Process Biochemistry, pp. 36–41 (Aug./Sep. 1980).

Farber et al., "the 3.0 Å crystal structure of xylose isomerase from *Streptomyces olivochromogenes*", *Protein Eng.* 1:459–466 (1987).

Rey et al., "Structure Analysis of the 2.8 Å Model of Xylose Isomerase From *Actinoplanes missouriensis*", *Proteins* 4:165–172 (1987).

Henrick et al., "Comparison of backbone structures of glucose isomerase from *Streptomyces and Arthrobacter*", *Protein Eng.* 1:467–475 (1987).

Callens et al., "D-Xylose isomerase from *Streptomyces violaceoruber*: structural and catalytic roles of bivalent metal ions", *Enzyme Microb. Technol.* 10:695–700 (1988).

R. van Tilbert, Thesis entitled "Engineering Aspects of Biocatalysts in Industrial Starch Conversion Technology", Delftse Universitaire Pers (1983).

```
Am1   1
Amp   1
Sv1   1
Smu   1
Sth   1
Art   1
Bsu   1                                                    MSVQATRED KF SFG LWTVGWQ AR.DAFGDATR
Eco   1                                                    MSLQATPDD KF SFG LWTVGWQ AR.DAFGDATR
Lxy   1                                                    MNYQPTPED RF TFG LWTVGWQ GR.DPFGDATR
                                                           MSFQPTPED RF TFG LWTVGWQ GR.DPFGDATR
                                                           MSYQPTPED RF SFG LWTVGWQ GR.DPFGDATR
                                                           MSVQPTPAD HF TFG LWTVGWT GA.DPFGVATR
      MAQSHSSSVNYFGSVNKVVFEGKASTNPLAFKYYNPQEVIGGKTMKEHLRFSIAYWH TFTADGTD VF GAA TMQRPWD HY.KGM.DLAR
          MQAYFDQLDRVRYEGSKSSNPLAFRHYNPDELVLGKRMEEHLRFAACYWH TFCWNGAD MF GVG AFNRPWQ QPGEAL.ALAK
             MAYFNDIAPIKYEGTKTKNMFAFRHYNPEEVVAGKTMEEQLHFALAFWH TITMDGSD PF GGA TMERPWD LEGGSELDRAH

Am1  31  TAL DPV.EAVH KLAEIG A YGI T FHDDDLVPE GS D....AQTRDGI IAGFKKALDE TG LIV PMVTT NLFTHPVFKD GGFTSN DRSV
Amp  31  PVL DPI.EAVH KLAEIG A YGV T FHDDDLVPF GA D....AATRDGI VAGFSKALDE TG LIV PMVTT NLFTHPVFKD GGFTSW DRSV
Sv1  31  QAL DPA.ESVR RLSELG A YGV T FHDDDLIPF GS S....DTERESH IKRFRQALDA TG MKV PMATT NLFTHPVFKD GAFTAN DRDV
Smu  31  PAL DPV.ETVQ RLAELG A YGV T FHDDDLIPF GS S....DTERESH IKRFRQALDA TG MTV PMATT NLFTHPVFKD GGFTAN DRDV
Sth  31  RPL DPV.GTVQ RLAELG A YGV T FHDDDLIPF GA S....EAEREAH VKRFRQALDA TG MTV PMATT NLFTHPVFKD GAFTAN DRDV
Art  31  KNL DPV.EAVH KLAELG A YGI T FHDNDLIPF DA T....EAEREKI LGDFNQALKD TG LKV PMVTT NLFSHPVFKD GGFTSN DRSI
Bsu  88  ARV EAAFEMFE KL...D A PFF A FHDRDIAPE GS TLKETNQNLDII VGMIKDYMRD SN VKL LWNTA NMFTNPRFVH GAATSC NADV
Eco  80  RKA DVAFEFFH KL...H V PFY C FHDVDSPE GA SLKEYINNFAQM VDVLAGKQEE TG VKL LWGTA NCFTNPRYGA GAATNP DPEV
Lxy  80  RRV DAFFEIAE KL...G V KYY C FHDIDIAPT GN SLKEFYANLDEI TDHLLEKQKA TG IKL LWNTA NMFSNPRYMN GVSTSN RAEV

Am1  111  RRYAIRKVLR QMDLGAELG A KTLVLW GGRE GAEYDSAK DV SAALDRYREA LNLLAQYSED RG YGL RFAIE PKPNEPRGDI
Amp  111  RRYAIRKVLR QMDLGAELG A KTLVLW GGRE GAEYDSAK DV GAALDRYREA LNLLAQYSED QG YGL RFAIE PKPNEPRGDI
Sv1  111  RRYALRKTIR NIDLAVELG A SVYVAW GGRE GAESGAAK DV RDALDRMKEA FDLLGEYVTE QG YDL KFAIE PKPNEPRGDI
Smu  111  RRYALRKTIR NIDLAAELG A KTYVAW GGRE GAESGGAK DV RDALDRMKEA FDLLGEYVTA QG YDL HFAIE PKPNEPRGDI
Sth  111  RRYALRKTIR NIDLAVELG A RTYVAW GGRE GAESGAAK DV RAALDRMKEA FDLLGEYVTS QG YDI RFAIE PKPNEPRGDI
Art  111  RRFALAKVLH NIDLAAEMG A ETFVMW GGRE GSEYDGSK DL AAALDRMREG VDTAAGYIKD KG YNL RIALE PKPNEPRGDI
Bsu  168  FAYAAQVKK GLETAKELG A ENYVFW GGRE GYETLLNT DL KFELDNLARF MHMAVDYAKE IE YTG QFLIE PKPKEPTTHQ
Eco  162  FSWAATQVVT AMEATHKLG L ENYVLW GGRE GYETLLNT DL RQEREQLGRF MQMVEHKHK IG FQG TLLIE PKPQEPTKHQ
Lxy  162  FAYGAAQVKK GLELSKKLG G ENYVFW GGRE GYESLLNT DM GLEMDHMAKF FHLAIDYAKS IN HLP IFLIE PKPKEPMTHQ
```

FIG. 2A

```
Ami 191  LLP TAGHAIA FVQ ELERPE L FGINPET GHE QMSNL NFTQG IAQALWHK K L FHIDL NGQHG .PKFDQDLVFG HG DLLNAFSL
Amp 191  LLP TAGHAIA FVQ ELERPE L FGINPET GHE QMSNL NFTQG IAQALWHK K L FHIDL NGQHG .PKFDQDLVFG HG DLLNAFSL
Svi 191  LLP TVGHALA FIE RLERPE L YGVNPEV GHE QMAGL NFPHG IAQALWAG K L FHIDL NGQSG .IKYDQDLRFG AG DLRAAFWL
Smu 191  LLP TVGHALA FIE RLERPE L YGVNPEV GHE QMAGL NFPHG IAQALWAG K L FHIDL NGQSG .IKYDQDLRFG AG DLRAAFWL
Sth 191  LLP TVGHALA FIE RLERPE L FGVNPEV GHE QMAGL NFPHG IAQALWAG K L FHIDL NGQSG .IKYDQDLRFG AG DLRAAFWL
Art 191  FLP TVGHGLA FIE QLEHGD I VGLNPET GHE QMAGL NFTHG IAQALWAE K L FHIDL NGQRG .IKYDQDLVFG HG DLTSAFFT
Bsu 248  YDT DAATTIA FLK QYGLDN H FKLNLEA NHA TLAGH TFEHE LRMARVHG L L GSVDA NQGHP LLGWDTDE.FP TD LYSTTLAM
Eco 242  YDY DAATVYG FLK QFGLEK E IKLNIEA NHA TLAGH SFHHE IATAIALG L F GSVDA NRGDA QLGWDTDQ.FP NS VEENALVM
Lxy 242  YDF DSATALA FLQ KYDLDK Y FKLNLET NHA WLAGH TFEHE LNTARTFN A L GSJDA NQGNY LLGWDTDE.FP TL VIDITLAM

Ami 271  VDLLE NG.PDG APAYDGP RHF D YKPSRT..E DY DGVWESAKAN IRMYLLLKER AKAFRA DPEV QEALAASKVA ELKTPTLNPG
Amp 271  VDLLE NG.PDG GPAYDGP RHF D YKPSRT..E DF DGVWESAKDN IRMYLLLKER AKAFRA DPEV QAALAESKVD ELRTPTLNPG
Svi 271  VDLLE RA...G ...YAGP RHF D FKPPRT..E DF DGVWASAAGC MRNYLILKDR AAAFRA DPQV QEALAAARLD ELARPT..AE
Smu 271  VDLLE TA...G ...YEGP RHF D FKPPRT..E DF DGVWASAAGC MRNYLILKDR AAAFRA DPEV QEALRAARLD QLAQPT..AA
Sth 271  VDLLE SS...G ...YDGP RHF D FKPPRT..E DL DGVWASAAGC MRNYLILKER SAAFRA DPEV QEALRASRLD QLAQPT..AA
Art 271  VDLLE NGFPNG GPKYTGP RHF D YKPSRT..D GY DGVWDSAKAN MSMYLLLKER ALAFRA DPEV QEAMKTSGVF ELGETTLNAG
Bsu 328  YEILQ NGGL.G ....SGG LNF D AKVRRSSFE PD DLVYAHIAGM DAFARGLKVA HKLI.E DRVF EDVIQHRYRS F.TEGIGLEI
Eco 322  YEILK AGGF.T ....TGG LNF D AKVRRQSTD KY DLFYGHIGAM DTMALALKIA ARMI.E DGEL DKRIAQRYSG W.NSELGQQI
Lxy 322  HQILL NGGL.G ....KGG INF D AKVRRTSFK AE DLILAHIAGM DTYARALKGA AAII.E DKFL SDIVDERYSS YRNTEVGQSI

Ami 351  EGYAELLADR SAFED.Y..DAD  AVGAKGFGFVK .LNQLAIEHLL GAR
Amp 351  ETYADLLADR SAFED.Y..DAD  AVGAKGYGFVK .LNQLAIDHLL GAR
Svi 344  DGLAALLADR SAYDT.F..DVD  AAAARGMAFEH .LDQLAMDHLL GAR
Smu 344  DGLDALLADR AAFED.F..DVD  AAAARGMAFEH .LDQLAMDHLL GARG
Sth 348  DGLQ
Art 352  ESAADLMNDS ASFAG.G..DAE  AAAERNFAFIR .LNQLAIEHLL GSR
Bsu 404  TEGRANFHTL EQYALNNK.TIK  NESGRQERLKP ILNQ
Eco 380  LKGQMSLADL AKYAQEHHLSPV  HQSGRQEQLEN LVNHYLFDK
Lxy 380  ENGTATFESL AAFALEYGDDIE  LDSNHLEYIKS VLNDYLV
```

FIG. 2B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 394 amino acids
( B ) TYPE: amino acid
( C ) STRANDEDNESS: single
( D ) TOPOLOGY: linear ( x i ) SEQUENCE DESCRIPTION: SEQ ID NO:1:

```
Met Ser Val Gln Ala Thr Arg Glu Asp Lys Phe Ser Phe Gly Leu Trp
 1               5                  10                  15

Thr Val Gly Trp Gln Ala Arg Asp Ala Phe Gly Asp Ala Thr Arg Thr
            20                  25                  30

Ala Leu Asp Pro Val Glu Ala Val His Lys Leu Ala Glu Ile Gly Ala
            35                  40                  45

Tyr Gly Ile Thr Phe His Asp Asp Leu Val Pro Phe Gly Ser Asp
 50                      55                  60

Ala Gln Thr Arg Asp Gly Ile Ile Ala Gly Phe Lys Lys Ala Leu Asp
 65                      70                  75                  80

Glu Thr Gly Leu Ile Val Pro Met Val Thr Thr Asn Leu Phe Thr His
                    85                  90                  95

Pro Val Phe Lys Asp Gly Phe Thr Ser Asn Asp Arg Ser Val Arg
                100                 105                 110

Arg Tyr Ala Ile Arg Lys Val Leu Arg Gln Met Asp Leu Gly Ala Glu
            115                 120                 125

Leu Gly Ala Lys Thr Leu Val Leu Trp Gly Gly Arg Glu Gly Ala Glu
    130                 135                 140

Tyr Asp Ser Ala Lys Asp Val Ser Ala Ala Leu Asp Arg Tyr Arg Glu
145                 150                 155                 160

Ala Leu Asn Leu Leu Ala Gln Tyr Ser Glu Asp Arg Gly Tyr Gly Leu
                165                 170                 175

Arg Phe Ala Ile Glu Pro Lys Pro Asn Glu Pro Arg Gly Asp Ile Leu
            180                 185                 190

Leu Pro Thr Ala Gly His Ala Ile Ala Phe Val Gln Glu Leu Glu Arg
        195                 200                 205

Pro Glu Leu Phe Gly Ile Asn Pro Glu Thr Gly His Glu Gln Met Ser
    210                 215                 220

Asn Leu Asn Phe Thr Gln Gly Ile Ala Gln Ala Leu Trp His Lys Lys
225                 230                 235                 240

Leu Phe His Ile Asp Leu Asn Gly Gln His Gly Pro Lys Phe Asp Gln
                245                 250                 255

Asp Leu Val Phe Gly His Gly Asp Leu Leu Asn Ala Phe Ser Leu Val
                260                 265                 270

Asp Leu Leu Glu Asn Gly Pro Asp Gly Ala Pro Ala Tyr Asp Gly Pro
        275                 280                 285

Arg His Phe Asp Tyr Lys Pro Ser Arg Thr Glu Asp Tyr Asp Gly Val
    290                 295                 300

Trp Glu Ser Ala Lys Ala Asn Ile Arg Met Tyr Leu Leu Leu Lys Glu
305                 310                 315                 320

Arg Ala Lys Ala Phe Arg Ala Asp Pro Glu Val Gln Glu Ala Leu Ala
                325                 330                 335

Ala Ser Lys Val Ala Glu Leu Lys Thr Pro Thr Leu Asn Pro Gly Glu
```

|     |     |     |     |     | 340 |     |     |     |     |     | 345 |     |     |     |     |     | 350 |     |
| --- | --- | --- | --- | --- | --- | --- | --- | --- | --- | --- | --- | --- | --- | --- | --- | --- | --- | --- |

Gly Tyr Ala Glu Leu Leu Ala Asp Arg Ser Ala Phe Glu Asp Tyr Asp
            355                    360             365

Ala Asp Ala Val Gly Ala Lys Gly Phe Gly Phe Val Lys Leu Asn Gln
        370             375             380

Leu Ala Ile Glu His Leu Leu Gly Ala Arg
385                 390

( 2 ) INFORMATION FOR SEQ ID NO:2:

( i ) SEQUENCE CHARACTERISTICS:
        ( A ) LENGTH: 394 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Met Ser Leu Gln Ala Thr Pro Asp Asp Lys Phe Ser Phe Gly Leu Trp
1               5                   10                  15

Thr Val Gly Trp Gln Ala Arg Asp Ala Phe Gly Asp Ala Thr Arg Pro
            20                  25                  30

Val Leu Asp Pro Ile Glu Ala Val His Lys Leu Ala Glu Ile Gly Ala
        35                  40                  45

Tyr Gly Val Thr Phe His Asp Asp Leu Val Pro Phe Gly Ala Asp
    50                  55                  60

Ala Ala Thr Arg Asp Gly Ile Val Ala Gly Phe Ser Lys Ala Leu Asp
65              70                  75                  80

Glu Thr Gly Leu Ile Val Pro Met Val Thr Thr Asn Leu Phe Thr His
                85                  90                  95

Pro Val Phe Lys Asp Gly Gly Phe Thr Ser Asn Asp Arg Ser Val Arg
            100                 105                 110

Arg Tyr Ala Ile Arg Lys Val Leu Arg Gln Met Asp Leu Gly Ala Glu
        115                 120                 125

Leu Gly Ala Lys Thr Leu Val Leu Trp Gly Gly Arg Glu Gly Ala Glu
130                 135                 140

Tyr Asp Ser Ala Lys Asp Val Gly Ala Ala Leu Asp Arg Tyr Arg Glu
145             150                 155                 160

Ala Leu Asn Leu Leu Ala Gln Tyr Ser Glu Asp Gln Gly Tyr Gly Leu
                165                 170                 175

Pro Phe Ala Ile Glu Pro Lys Pro Asn Glu Pro Arg Gly Asp Ile Leu
            180                 185                 190

Leu Pro Thr Ala Gly His Ala Ile Ala Phe Val Gln Glu Leu Glu Arg
        195                 200                 205

Pro Glu Leu Phe Gly Ile Asn Pro Glu Thr Gly His Glu Gln Met Ser
    210                 215                 220

Asn Leu Asn Phe Thr Gln Gly Ile Ala Gln Ala Leu Trp His Lys Lys
225                 230                 235                 240

Leu Phe His Ile Asp Leu Asn Gly Gln His Gly Pro Lys Phe Asp Gln
                245                 250                 255

Asp Leu Val Phe Gly His Gly Asp Leu Leu Asn Ala Phe Ser Leu Val
            260                 265                 270

Asp Leu Leu Glu Asn Gly Pro Asp Gly Gly Pro Ala Tyr Asp Gly Pro
        275                 280                 285

Arg His Phe Asp Tyr Lys Pro Ser Arg Thr Glu Asp Phe Asp Gly Val
    290                 295                 300

Trp Glu Ser Ala Lys Asp Asn Ile Arg Met Tyr Leu Leu Leu Lys Glu
305                 310                 315                 320

```
        Arg  Ala  Lys  Ala  Phe  Arg  Ala  Asp  Pro  Glu  Val  Gln  Ala  Ala  Leu  Ala
                       325                      330                           335

Glu  Ser  Lys  Val  Asp  Glu  Leu  Arg  Thr  Pro  Thr  Leu  Asn  Pro  Gly  Glu
                       340                      345                     350

Thr  Tyr  Ala  Asp  Leu  Leu  Ala  Asp  Arg  Ser  Ala  Phe  Glu  Asp  Tyr  Asp
                       355                      360                363

Ala  Asp  Ala  Val  Gly  Ala  Lys  Gly  Tyr  Gly  Phe  Val  Lys  Leu  Asn  Gln
             370                      375                     380

Leu  Ala  Ile  Asp  His  Leu  Leu  Gly  Ala  Arg
        385                      390
```

( 2 ) INFORMATION FOR SEQ ID NO:3:

( i ) SEQUENCE CHARACTERISTICS:
        ( A ) LENGTH: 395 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
        Met  Ser  Val  Gln  Pro  Thr  Pro  Ala  Asp  His  Phe  Thr  Phe  Gly  Leu  Trp
        1              5                        10                      15

Thr  Val  Gly  Trp  Thr  Gly  Ala  Asp  Pro  Phe  Gly  Val  Ala  Thr  Arg  Lys
                       20                       25                      30

Asn  Leu  Asp  Pro  Val  Glu  Ala  Val  His  Lys  Leu  Ala  Glu  Leu  Gly  Ala
                       35                       40                      45

Tyr  Gly  Ile  Thr  Phe  His  Asp  Asn  Asp  Leu  Ile  Pro  Phe  Asp  Ala  Thr
             50                            55                      60

Glu  Ala  Glu  Arg  Glu  Lys  Ile  Leu  Gly  Asp  Phe  Asn  Gln  Ala  Leu  Lys
        65                       70                       75                      80

Asp  Thr  Gly  Leu  Lys  Val  Pro  Met  Val  Thr  Thr  Asn  Leu  Phe  Ser  His
                            85                       90                      95

Pro  Val  Phe  Lys  Asp  Gly  Gly  Phe  Thr  Ser  Asn  Asp  Arg  Ser  Ile  Arg
                       100                     105                     110

Arg  Phe  Ala  Leu  Ala  Lys  Val  Leu  His  Asn  Ile  Asp  Leu  Ala  Ala  Glu
                       115                     120                     125

Met  Gly  Ala  Glu  Thr  Phe  Val  Met  Trp  Gly  Gly  Arg  Glu  Gly  Ser  Glu
             130                          135                     140

Tyr  Asp  Gly  Ser  Lys  Asp  Leu  Ala  Ala  Ala  Leu  Asp  Arg  Met  Arg  Glu
        145                     150                     155                     160

Gly  Val  Asp  Thr  Ala  Ala  Gly  Tyr  Ile  Lys  Asp  Lys  Gly  Tyr  Asn  Leu
                            165                     170                     175

Arg  Ile  Ala  Leu  Glu  Pro  Lys  Pro  Asn  Glu  Pro  Arg  Gly  Asp  Ile  Phe
                       180                     185                     190

Leu  Pro  Thr  Val  Gly  His  Gly  Leu  Ala  Phe  Ile  Glu  Gln  Leu  Glu  His
                       195                     200                     205

Gly  Asp  Ile  Val  Gly  Leu  Asn  Pro  Glu  Thr  Gly  His  Glu  Gln  Met  Ala
             210                     215                     220

Gly  Leu  Asn  Phe  Thr  His  Gly  Ile  Ala  Gln  Ala  Leu  Trp  Ala  Glu  Lys
        225                     230                     235                     240

Leu  Phe  His  Ile  Asp  Leu  Asn  Gly  Gln  Arg  Gly  Ile  Lys  Tyr  Asp  Gln
                            245                     250                     255

Asp  Leu  Val  Phe  Gly  His  Gly  Asp  Leu  Thr  Ser  Ala  Phe  Phe  Thr  Val
                       260                     265                     270

Asp  Leu  Leu  Glu  Asn  Gly  Phe  Pro  Asn  Gly  Gly  Pro  Lys  Tyr  Thr  Gly
                       275                     280                     285

Pro  Arg  His  Phe  Asp  Tyr  Lys  Pro  Ser  Arg  Thr  Asp  Gly  Tyr  Asp  Gly
             290                     295                     300
```

```
Val Trp Asp Ser Ala Lys Ala Asn Met Ser Met Tyr Leu Leu Leu Lys
305                 310                 315                 320

Glu Arg Ala Leu Ala Phe Arg Ala Asp Pro Glu Val Gln Glu Ala Met
                325                 330                 335

Lys Thr Ser Gly Val Phe Glu Leu Gly Glu Thr Thr Leu Asn Ala Gly
                340                 345                 350

Glu Ser Ala Ala Asp Leu Met Asn Asp Ser Ala Ser Phe Ala Gly Phe
            355                 360                 365

Asp Ala Glu Ala Ala Ala Glu Arg Asn Phe Ala Phe Ile Arg Leu Asn
        370                 375                 380

Gln Leu Ala Ile Glu His Leu Leu Gly Ser Arg
385                 390                 395
```

( 2 ) INFORMATION FOR SEQ ID NO:4:

( i ) SEQUENCE CHARACTERISTICS:
        ( A ) LENGTH: 440 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met Ala Gln Ser His Ser Ser Ser Val Asn Tyr Phe Gly Ser Val Asn
1               5                   10                  15

Lys Val Val Phe Glu Gly Lys Ala Ser Thr Asn Pro Leu Ala Phe Lys
                20                  25                  30

Tyr Tyr Asn Pro Gln Glu Val Ile Gly Gly Lys Thr Met Lys Glu His
            35                  40                  45

Leu Arg Phe Ser Ile Ala Tyr Trp His Thr Phe Thr Ala Asp Gly Thr
50                  55                  60

Asp Val Phe Gly Ala Ala Thr Met Gln Arg Pro Trp Asp His Tyr Lys
65                  70                  75                  80

Gly Met Asp Leu Ala Arg Ala Arg Val Glu Ala Ala Phe Glu Met Phe
                85                  90                  95

Glu Lys Leu Asp Ala Pro Phe Phe Ala Phe His Asp Arg Asp Ile Ala
                100                 105                 110

Pro Glu Gly Ser Thr Leu Lys Glu Thr Asn Gln Asn Leu Asp Ile Ile
            115                 120                 125

Val Gly Met Ile Lys Asp Tyr Met Arg Asp Ser Asn Val Lys Leu Leu
130                 135                 140

Trp Asn Thr Ala Asn Met Phe Thr Asn Pro Arg Phe Val His Gly Ala
145                 150                 155                 160

Ala Thr Ser Cys Asn Ala Asp Val Phe Ala Tyr Ala Ala Ala Gln Val
                165                 170                 175

Lys Lys Gly Leu Glu Thr Ala Lys Glu Leu Gly Ala Glu Asn Tyr Val
                180                 185                 190

Phe Trp Gly Gly Arg Glu Gly Tyr Glu Thr Leu Leu Asn Thr Asp Leu
            195                 200                 205

Lys Phe Glu Leu Asp Asn Leu Ala Arg Phe Met His Met Ala Val Asp
210                 215                 220

Tyr Ala Lys Glu Ile Glu Tyr Thr Gly Gln Phe Leu Ile Glu Pro Lys
225                 230                 235                 240

Pro Lys Glu Pro Thr Thr His Gln Tyr Asp Thr Asp Ala Ala Thr Thr
                245                 250                 255

Ile Ala Phe Leu Lys Gln Tyr Gly Leu Asp Asn His Phe Lys Leu Asn
            260                 265                 270

Leu Glu Ala Asn His Ala Thr Leu Ala Gly His Thr Phe Glu His Glu
```

```
                              275                        280                        285
        Leu  Arg  Met  Ala  Arg  Val  His  Gly  Leu  Leu  Gly  Ser  Val  Asp  Ala  Asn
             290                      295                      300

Gln  Gly  His  Pro  Leu  Leu  Gly  Trp  Asp  Thr  Asp  Glu  Phe  Pro  Thr  Asp
        305                      310                      315                      320

Leu  Tyr  Ser  Thr  Thr  Leu  Ala  Met  Tyr  Glu  Ile  Leu  Gln  Asn  Gly  Gly
                            325                      330                      335

Leu  Gly  Ser  Gly  Gly  Leu  Asn  Phe  Asp  Ala  Lys  Val  Arg  Arg  Ser  Ser
                       340                      345                      350

Phe  Glu  Pro  Asp  Asp  Leu  Val  Tyr  Ala  His  Ile  Ala  Gly  Met  Asp  Ala
                  355                      360                      365

Phe  Ala  Arg  Gly  Leu  Lys  Val  Ala  His  Lys  Leu  Ile  Glu  Asp  Arg  Val
             370                      375                      380

Phe  Glu  Asp  Val  Ile  Gln  His  Arg  Tyr  Arg  Ser  Phe  Thr  Glu  Gly  Ile
        385                      390                      395                      400

Gly  Leu  Glu  Ile  Thr  Glu  Gly  Arg  Ala  Asn  Phe  His  Thr  Leu  Glu  Gln
                            405                      410                      415

Tyr  Ala  Leu  Asn  Asn  Lys  Thr  Ile  Lys  Asn  Glu  Ser  Gly  Arg  Gln  Glu
                       420                      425                      430

Arg  Leu  Lys  Pro  Ile  Leu  Asn  Gln
                  435                      440
```

( 2 ) INFORMATION FOR SEQ ID NO:5:

( i ) SEQUENCE CHARACTERISTICS:
        ( A ) LENGTH: 440 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
        Met  Gln  Ala  Tyr  Phe  Asp  Gln  Leu  Asp  Arg  Val  Arg  Tyr  Glu  Gly  Ser
        1                   5                        10                       15

Lys  Ser  Ser  Asn  Pro  Leu  Ala  Phe  Arg  His  Tyr  Asn  Pro  Asp  Glu  Leu
                       20                       25                       30

Val  Leu  Gly  Lys  Arg  Met  Glu  Glu  His  Leu  Arg  Phe  Ala  Ala  Cys  Tyr
                  35                       40                       45

Trp  His  Thr  Phe  Cys  Trp  Asn  Gly  Ala  Asp  Met  Phe  Gly  Val  Gly  Ala
             50                       55                       60

Phe  Asn  Arg  Pro  Trp  Gln  Gln  Pro  Gly  Glu  Ala  Leu  Ala  Leu  Ala  Lys
        65                       70                       75                       80

Arg  Lys  Ala  Asp  Val  Ala  Phe  Glu  Phe  Phe  His  Lys  Leu  His  Val  Pro
                            85                       90                       95

Phe  Tyr  Cys  Phe  His  Asp  Val  Asp  Val  Ser  Pro  Glu  Gly  Ala  Ser  Leu
                       100                      105                      110

Lys  Glu  Tyr  Ile  Asn  Asn  Phe  Ala  Gln  Met  Val  Asp  Val  Leu  Ala  Gly
                  115                      120                      125

Lys  Gln  Glu  Glu  Ser  Gly  Val  Lys  Leu  Leu  Trp  Gly  Thr  Ala  Asn  Cys
             130                      135                      140

Phe  Thr  Asn  Pro  Arg  Tyr  Gly  Ala  Gly  Ala  Ala  Thr  Asn  Pro  Asp  Pro
        145                      150                      155                      160

Glu  Val  Phe  Ser  Trp  Ala  Ala  Thr  Gln  Val  Val  Thr  Ala  Met  Glu  Ala
                            165                      170                      175

Thr  His  Lys  Leu  Gly  Gly  Glu  Asn  Tyr  Val  Leu  Trp  Gly  Gly  Arg  Glu
                       180                      185                      190

Gly  Tyr  Glu  Thr  Leu  Leu  Asn  Thr  Asp  Leu  Arg  Gln  Glu  Arg  Glu  Gln
                  195                      200                      205
```

```
Leu  Gly  Arg  Phe  Met  Gln  Met  Val  Val  Glu  His  Lys  His  Lys  Ile  Gly
     210                 215                 220

Phe  Gln  Gly  Thr  Leu  Leu  Ile  Glu  Pro  Lys  Pro  Gln  Glu  Pro  Thr  Lys
225                      230                 235                      240

His  Gln  Tyr  Asp  Tyr  Asp  Ala  Ala  Thr  Val  Tyr  Gly  Phe  Leu  Lys  Gln
                    245                 250                           255

Phe  Gly  Leu  Glu  Lys  Glu  Ile  Lys  Leu  Asn  Ile  Glu  Ala  Asn  His  Ala
               260                      265                 270

Thr  Leu  Ala  Gly  His  Ser  Phe  His  Glu  Ile  Ala  Thr  Ala  Ile  Ala
          275                      280                 285

Leu  Gly  Leu  Phe  Gly  Ser  Val  Asp  Ala  Asn  Arg  Gly  Asp  Ala  Gln  Leu
     290                      295                      300

Gly  Trp  Asp  Thr  Asp  Gln  Phe  Pro  Asn  Ser  Val  Glu  Glu  Asn  Ala  Leu
305                      310                 315                           320

Val  Met  Tyr  Glu  Ile  Leu  Lys  Ala  Gly  Gly  Phe  Thr  Thr  Gly  Gly  Leu
                    325                 330                           335

Asn  Phe  Asp  Ala  Lys  Val  Arg  Arg  Gln  Ser  Thr  Asp  Lys  Tyr  Asp  Leu
               340                 345                 350

Phe  Tyr  Gly  His  Ile  Gly  Ala  Met  Asp  Thr  Met  Ala  Leu  Ala  Leu  Lys
          355                      360                 365

Ile  Ala  Ala  Arg  Met  Ile  Glu  Asp  Gly  Glu  Leu  Asp  Lys  Arg  Ile  Ala
     370                      375                 380

Gln  Arg  Tyr  Ser  Gly  Trp  Asn  Ser  Glu  Leu  Gly  Gln  Gln  Ile  Leu  Lys
385                      390                      395                      400

Gly  Gln  Met  Ser  Leu  Ala  Asp  Leu  Ala  Lys  Tyr  Ala  Gln  Glu  His  His
                    405                      410                      415

Leu  Ser  Pro  Val  His  Gln  Ser  Gly  Arg  Gln  Glu  Gln  Leu  Glu  Asn  Leu
               420                      425                      430

Val  Asn  His  Tyr  Leu  Phe  Asp  Lys
          435                 440
```

( 2 ) INFORMATION FOR SEQ ID NO:6:

( i ) SEQUENCE CHARACTERISTICS:
        ( A ) LENGTH: 439 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Met  Ala  Tyr  Phe  Asn  Asp  Ile  Ala  Pro  Ile  Lys  Tyr  Glu  Gly  Thr  Lys
1                   5                   10                          15

Thr  Lys  Asn  Met  Phe  Ala  Phe  Arg  His  Tyr  Asn  Pro  Glu  Glu  Val  Val
               20                  25                      30

Ala  Gly  Lys  Thr  Met  Glu  Glu  Gln  Leu  His  Phe  Ala  Leu  Ala  Phe  Trp
          35                  40                      45

His  Thr  Ile  Thr  Met  Asp  Gly  Ser  Asp  Pro  Phe  Gly  Gly  Ala  Thr  Met
     50                       55                      60

Glu  Arg  Pro  Trp  Asp  Leu  Glu  Gly  Gly  Ser  Glu  Leu  Asp  Arg  Ala  His
65                       70                  75                           80

Arg  Arg  Val  Asp  Ala  Phe  Phe  Glu  Ile  Ala  Glu  Lys  Leu  Gly  Val  Lys
                    85                  90                           95

Tyr  Tyr  Cys  Phe  His  Asp  Ile  Asp  Ile  Ala  Pro  Thr  Gly  Asn  Ser  Leu
               100                 105                      110

Lys  Glu  Phe  Tyr  Ala  Asn  Leu  Asp  Glu  Ile  Thr  Asp  His  Leu  Leu  Glu
          115                      120                 125

Lys  Gln  Lys  Ala  Thr  Gly  Ile  Lys  Leu  Leu  Trp  Asn  Thr  Ala  Asn  Met
     130                      135                 140
```

```
Phe  Ser  Asn  Pro  Arg  Tyr  Met  Asn  Gly  Val  Ser  Thr  Ser  Asn  Arg  Ala
145                 150                      155                           160

Glu  Val  Phe  Ala  Tyr  Gly  Ala  Ala  Gln  Val  Lys  Lys  Gly  Leu  Glu  Leu
                    165                      170                      175

Ser  Lys  Lys  Leu  Gly  Gly  Glu  Asn  Tyr  Val  Phe  Trp  Gly  Gly  Arg  Glu
               180                      185                      190

Gly  Tyr  Glu  Ser  Leu  Leu  Asn  Thr  Asp  Met  Gly  Leu  Glu  Met  Asp  His
          195                      200                      205

Met  Ala  Lys  Phe  Phe  His  Leu  Ala  Ile  Asp  Tyr  Ala  Lys  Ser  Ile  Asn
     210                      215                      220

His  Leu  Pro  Ile  Phe  Leu  Ile  Glu  Pro  Lys  Pro  Lys  Glu  Pro  Met  Thr
225                      230                      235                      240

His  Gln  Tyr  Asp  Phe  Asp  Ser  Ala  Thr  Ala  Leu  Ala  Phe  Leu  Gln  Lys
                    245                      250                      255

Tyr  Asp  Leu  Asp  Lys  Tyr  Phe  Lys  Leu  Asn  Leu  Glu  Thr  Asn  His  Ala
               260                      265                      270

Trp  Leu  Ala  Gly  His  Thr  Phe  Glu  His  Glu  Leu  Asn  Thr  Ala  Arg  Thr
          275                      280                      285

Phe  Asn  Ala  Leu  Gly  Ser  Ile  Asp  Ala  Asn  Gln  Gly  Asn  Tyr  Leu  Leu
     290                      295                      300

Gly  Trp  Asp  Thr  Asp  Glu  Phe  Pro  Thr  Leu  Val  Ile  Asp  Ile  Thr  Leu
305                      310                      315                      320

Ala  Met  His  Gln  Ile  Leu  Leu  Asn  Gly  Gly  Leu  Gly  Lys  Gly  Gly  Ile
               325                      330                      335

Asn  Phe  Asp  Ala  Lys  Val  Arg  Arg  Thr  Ser  Phe  Lys  Ala  Glu  Asp  Leu
               340                      345                      350

Ile  Leu  Ala  His  Ile  Ala  Gly  Met  Asp  Thr  Tyr  Ala  Arg  Ala  Leu  Lys
          355                      360                      365

Gly  Ala  Ala  Ala  Ile  Ile  Glu  Asp  Lys  Phe  Leu  Ser  Asp  Ile  Val  Asp
370                      375                      380

Glu  Arg  Tyr  Ser  Ser  Tyr  Arg  Asn  Thr  Glu  Val  Gly  Gln  Ser  Ile  Glu
385                      390                      395                      400

Asn  Gly  Thr  Ala  Thr  Phe  Glu  Ser  Leu  Ala  Ala  Phe  Ala  Leu  Glu  Tyr
               405                      410                      415

Gly  Asp  Asp  Ile  Glu  Leu  Asp  Ser  Asn  His  Leu  Glu  Tyr  Ile  Lys  Ser
               420                      425                      430

Val  Leu  Asn  Asp  Tyr  Leu  Val
          435
```

( 2 ) INFORMATION FOR SEQ ID NO:7:

( i ) SEQUENCE CHARACTERISTICS:
        ( A ) LENGTH: 388 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Met  Ser  Phe  Gln  Pro  Thr  Pro  Glu  Asp  Arg  Phe  Thr  Phe  Gly  Leu  Trp
1                   5                        10                       15

Thr  Val  Gly  Trp  Gln  Gly  Arg  Asp  Pro  Phe  Gly  Asp  Ala  Thr  Arg  Pro
               20                       25                       30

Ala  Leu  Asp  Pro  Val  Glu  Thr  Val  Gln  Arg  Leu  Ala  Glu  Leu  Gly  Ala
          35                       40                       45

Tyr  Gly  Val  Thr  Phe  His  Asp  Asp  Leu  Ile  Pro  Phe  Gly  Ser  Ser
     50                       55                       60

Asp  Thr  Glu  Arg  Glu  Ser  His  Ile  Lys  Arg  Phe  Arg  Gln  Ala  Leu  Asp
```

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |

Ala Thr Gly Met Thr Val Pro Met Ala Thr Thr Asn Leu Phe Thr His
            85              90              95

Pro Val Phe Lys Asp Gly Gly Phe Thr Ala Asn Asp Arg Asp Val Arg
            100             105             110

Arg Tyr Ala Leu Arg Lys Thr Ile Gly Asn Ile Asp Leu Ala Ala Glu
            115             120             125

Leu Gly Ala Lys Thr Tyr Val Ala Trp Gly Gly Arg Glu Gly Ala Glu
            130             135             140

Ser Gly Gly Ala Lys Asp Val Arg Asp Ala Leu Asp Arg Met Lys Glu
145             150             155             160

Ala Phe Asp Leu Leu Gly Glu Tyr Val Thr Ala Gln Gly Tyr Asp Leu
                165             170             175

Arg Phe Ala Ile Glu Pro Lys Pro Asn Glu Pro Arg Gly Asp Ile Leu
            180             185             190

Leu Pro Thr Val Gly His Ala Leu Ala Phe Ile Glu Arg Leu Glu Arg
            195             200             205

Pro Glu Leu Tyr Gly Val Asn Pro Glu Val Gly His Glu Gln Met Ala
    210             215             220

Gly Leu Asn Phe Pro His Gly Ile Ala Gln Ala Leu Trp Ala Gly Lys
225             230             235             240

Leu Phe His Ile Asp Leu Asn Gly Gln Ser Gly Ile Lys Tyr Asp Gln
                245             250             255

Asp Leu Arg Phe Gly Ala Gly Asp Leu Arg Ala Ala Phe Trp Leu Val
            260             265             270

Asp Leu Leu Glu Thr Ala Gly Tyr Glu Gly Pro Arg His Phe Asp Phe
            275             280             285

Lys Pro Pro Arg Thr Glu Asp Phe Asp Gly Val Trp Ala Ser Ala Ala
    290             295             300

Gly Cys Met Arg Asn Tyr Leu Ile Leu Lys Asp Arg Ala Ala Ala Phe
305             310             315             320

Arg Ala Asp Pro Glu Val Gln Glu Ala Leu Arg Ala Ala Arg Leu Asp
            325             330             335

Gln Leu Ala Gln Pro Thr Ala Ala Asp Gly Leu Asp Ala Leu Leu Ala
            340             345             350

Asp Arg Ala Ala Phe Glu Asp Phe Asp Val Asp Ala Ala Ala Ala Arg
            355             360             365

Gly Met Ala Phe Glu His Leu Asp Gln Leu Ala Met Asp His Leu Leu
            370             375             380

Gly Ala Arg Gly
385

( 2 ) INFORMATION FOR SEQ ID NO:8:

( i ) SEQUENCE CHARACTERISTICS:
         ( A ) LENGTH: 348 amino acids
         ( B ) TYPE: amino acid
         ( C ) STRANDEDNESS: single
         ( D ) TOPOLOGY: linear ( x i ) SEQUENCE DESCRIPTION: SEQ ID NO:8:

Met Ser Tyr Gln Pro Thr Pro Glu Asp Arg Phe Ser Phe Gly Leu Trp
1               5               10              15

Thr Val Gly Trp Gln Gly Arg Asp Pro Phe Gly Asp Ala Thr Arg Arg
            20              25              30

Pro Leu Asp Pro Val Gly Thr Val Gln Arg Leu Ala Glu Leu Gly Ala
            35              40              45

```
Tyr Gly Val Thr Phe His Asp Asp Leu Ile Pro Phe Gly Ala Ser
     50                  55                  60

Glu Ala Glu Arg Glu Ala His Val Lys Arg Phe Arg Gln Ala Leu Asp
 65              70                  75                      80

Ala Thr Gly Met Thr Val Pro Met Ala Thr Thr Asn Leu Phe Thr His
                 85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Arg Thr Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145             150                 155                     160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Phe Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ser Gly Tyr Asp Gly Pro Arg His Phe Asp Phe
        275                 280                 285

Lys Pro Pro Arg Thr Glu Asp Leu Asp Gly Val Trp Ala Ser Ala Ala
290                 295                 300

Gly Cys Met Arg Asn Tyr Leu Ile Leu Lys Glu Arg Ser Ala Ala Phe
305                 310                 315                 320

Arg Ala Asp Pro Glu Val Gln Glu Ala Leu Arg Ala Ser Arg Leu Asp
            325                 330                 335

Gln Leu Ala Gln Pro Thr Ala Ala Asp Gly Leu Gln
        340                 345
```

( 2 ) INFORMATION FOR SEQ ID NO:9:

( i ) SEQUENCE CHARACTERISTICS:
        ( A ) LENGTH: 387 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Met Asn Tyr Gln Pro Thr Pro Glu Asp Arg Phe Thr Phe Gly Leu Trp
 1               5                  10                  15

Thr Val Gly Trp Gln Gly Arg Asp Pro Phe Gly Asp Ala Thr Arg Gln
             20                 25                  30

Ala Leu Asp Pro Ala Glu Ser Val Arg Arg Leu Ser Glu Leu Gly Ala
            35                  40                  45

Tyr Gly Val Thr Phe His Asp Asp Leu Ile Pro Phe Gly Ser Ser
     50                  55                  60

Asp Thr Glu Arg Glu Ser His Ile Lys Arg Phe Arg Gln Ala Leu Asp
 65              70                  75                      80
```

```
Ala Thr Gly Met Lys Val Pro Met Ala Thr Thr Asn Leu Phe Thr His
            85                  90                    95
Pro Val Phe Lys Asp Gly Ala Phe Thr Ala Asn Asp Arg Asp Val Arg
            100                 105                110
Arg Tyr Ala Leu Arg Lys Thr Ile Arg Asn Ile Asp Leu Ala Val Glu
        115             120                     125
Leu Gly Ala Ser Val Tyr Val Ala Trp Gly Gly Arg Glu Gly Ala Glu
    130                 135                 140
Ser Gly Ala Ala Lys Asp Val Arg Asp Ala Leu Asp Arg Met Lys Glu
145                 150                 155                 160
Ala Phe Asp Leu Leu Gly Glu Tyr Val Thr Glu Gln Gly Tyr Asp Leu
            165                 170                     175
Lys Phe Ala Ile Glu Pro Lys Pro Asn Glu Pro Arg Gly Asp Ile Leu
            180                 185                 190
Leu Pro Thr Val Gly His Ala Leu Ala Phe Ile Glu Arg Leu Glu Arg
        195                 200                 205
Pro Glu Leu Tyr Gly Val Asn Pro Glu Val Gly His Glu Gln Met Ala
    210                 215                 220
Gly Leu Asn Phe Pro His Gly Ile Ala Gln Ala Leu Trp Ala Gly Lys
225                 230                 235                 240
Leu Phe His Ile Asp Leu Asn Gly Gln Ser Gly Ile Lys Tyr Asp Gln
            245                 250                     255
Asp Leu Arg Phe Gly Ala Gly Asp Leu Arg Ala Ala Phe Trp Leu Val
            260                 265                 270
Asp Leu Leu Glu Arg Ala Gly Tyr Ala Gly Pro Arg His Phe Asp Phe
        275                 280                 285
Lys Pro Pro Arg Thr Glu Asp Phe Asp Gly Val Trp Ala Ser Ala Ala
    290                 295                 300
Gly Cys Met Arg Asn Tyr Leu Ile Leu Lys Asp Arg Ala Ala Ala Phe
305                 310                 315                 320
Arg Ala Asp Pro Gln Val Gln Glu Ala Leu Ala Ala Ala Arg Leu Asp
            325                 330                     335
Glu Leu Ala Arg Pro Thr Ala Glu Asp Gly Leu Ala Ala Leu Leu Ala
        340                 345                 350
Asp Arg Ser Ala Tyr Asp Thr Phe Asp Val Asp Ala Ala Ala Ala Arg
        355                 360                 365
Gly Met Ala Phe Glu His Leu Asp Gln Leu Ala Met Asp His Leu Leu
    370                 375                 380
Gly Ala Arg
385
```

GLUCOSE ISOMERASES WITH AN ALTERED PH OPTIMUM

This application is a continuation, of application Ser. No. 07/637,399 filed Jan. 4, 1991.

TECHNICAL FIELD

The present invention relates to the application of protein engineering technology to improve the properties of metalloenzymes. A method for selecting amino acids which upon alteration will influence the pH-activity profile of metalloenzymes is provided. Said method is applied to glucose isomerase. The present invention also provides mutated glucose isomerase molecules with an altered pH optimum. Specifically the acidic flank of the pH-activity profile is shifted towards lower pH.

The present invention further provides recombinant glucose isomerases that advantageously can be applied in the production of fructose syrups, in particular high fructose corn syrups.

BACKGROUND OF THE INVENTION

Industrial application of glucose isomerase

In industrial starch degradation enzymes play an important role. The enzyme α-amylase is used for liquefaction of starch into dextrins with a polymerization degree of about 7–10. Subsequently the enzyme α-amyloglucosidase is used for saccharification which results in a syrup containing 92–96% glucose. The reversible isomerization of glucose into fructose is catalyzed by the enzyme glucose (or xylose) isomerase. The correct nomenclature of this enzyme is D-xylose-ketolisomerase (EC 5.3.1.5) due to the enzyme's preference for xylose. However, because of the enzyme's major application in the conversion of glucose to fructose it is commonly called glucose isomerase. The equilibrium constant for this isomerization is close to unity so under optimal process conditions about 50% of the glucose is converted. The equilibrium mixture of glucose and fructose is known as high fructose syrup.

Fructose is much sweeter to the human taste than glucose or sucrose which makes it an economically competitive sugar substitute.

Many microorganisms which were found to produce glucose isomerase, have been applied industrially. A detailed review of the industrial use of glucose isomerases has been given by Wen-Pin Chen in Process Biochemistry, 15 June/July (1980) 30–41 and August/September (1980) 36–41.

The Wen-Pin Chen reference describes culture conditions for the microorganisms, as well as recovery and purification methods for the enzyme. In addition it also summarizes the properties of glucose isomerases such as the substrate specificity, temperature optima and pH optima, heat stability and metal ion requirement.

Glucose isomerase requires a bivalent cation such as $Mg^{2+}$, $CO^{2+}$, $Mn^{2+}$ or a combination of these cations for its catalytic activity. Determination of 3D structures of different glucose isomerases has revealed the presence of two metal ions in the monomeric unit (Farber et al., Protein Eng. 1 (1987) 459–466; Rey et al., Proteins 4 (1987) 165–172; Henrick et al., Protein Eng. 1 (1987) 467–475).

Apart from a role in the catalytic mechanism, bivalent cations are also reported to increase the thermostability of some glucose isomerases (M. Callens et al. in Enzyme Microb. Technol. 1988 (10), 695–700). Furthermore, the catalytic activity of glucose isomerase is severely inhibited by $Ag^+$, $Hg^{2+}$, $Cu^{2+}$, $Zn^{2+}$ and $Ca^{2+}$.

Glucose isomerases usually have their pH optimum between 7.0 and 9.0. There are several reasons why it would be beneficial to use glucose isomerase at a lower pH value. Three of these reasons;

a) stability of the sugar molecules, b) adaptation both to previous and/or later process steps and c) stability of the enzyme, will be further described below to illustrate this.

a) Under alkaline conditions and at elevated temperatures the formation of coloured by-products and the production of a non-metabolizable sugar (D-Psicose) are a problem. The desired working pH should be around 6.0. Around this pH degradation of glucose and fructose would be minimal.

b) A lowered pH optimum is also desirable for glucose isomerase when this enzyme is to be used in combination with other enzymes, or between other enzymatic steps, for example in the manufacturing of high fructose syrups. In this process one of the other enzymatic steps, the saccharification by α-glucoamylase is performed at pH 4.5.

c) Most of the known glucose isomerases are applied at pH 7.5. This pH value is a compromise between a higher initial activity at higher pH and a better stability of the immobilized enzyme at lower pH, resulting in an optimal productivity at the pH chosen (R. v. Tilburg, Thesis: "Engineering aspects of Biocatalysts in Industrial Starch Conversion Technology", Delftse Universitaire Pers, 1983). Application of glucose isomerase at a pH lower than 7.5 could benefit from the longer half-life and, combined with an improved higher specific activity, would consequently increase the productivity of the immobilized enzyme at that lower pH.

From the above it can be concluded that there is need for glucose isomerases with a higher activity at lower pH values under process conditions.

Many microorganisms were screened for a glucose isomerase with a lower pH optimum. Despite many efforts, this approach did not lead to novel commercial glucose isomerases.

In order to be able to change pH-activity profile of glucose isomerases towards lower pH by protein engineering it is important to recognize the underlying effects which give rise to the rapid decrease in catalytic performance at acidic pH.

The role of metal ions in enzymes

Two different functions for metal ions in enzymes can be envisaged.

First of all metal ions can have a structural role. This means that they are involved in maintaining the proper 3D-structure and, therefore, contribute to the (thermo)stability of the enzyme molecule. An example of such a structural and stabilizing role is $Ca^{2+}$ in the subtilisin family of serine proteinases.

Secondly, metal ions can act as a cofactor in the catalytic mechanism. In this case the enzyme activity is strictly dependent upon the presence of the metal ion in the active site. The metal ion may for instance serve as a bridge between the enzyme and the substrate (e.g. $Ca^{2+}$ in phospholipase binds the phosphate group of the substrate) or it may activate water to become a powerful nucleophilic hydroxyl ion ($Zn^{2+}$—$OH^-$).

Examples are the $Zn^{2+}$-proteases such as thermolysin and carboxypeptidase, carbonic anhydrase ($Zn^{2+}$), phospholipase-$A_2$ ($Ca^{2+}$) staphylococcal nuclease ($Ca^{2+}$) and alkaline phosphatases ($Mg^{2+}$, $Ca^{2+}$). Examples of alpha/beta barrel enzymes which require cations to polarize a carboxyl or a carbonyl group in order to transfer hydrogen are glucose/xylose isomerase ($Mg^{2+}$), ribulose-1,5-biphosphate carboxylase/oxygenase (RUBISCO) ($Mg^{2+}$), enolase ($Mg^{2+}$), yeast aldolase ($Mg^{2+}$, $K^{1+}$), mandolate racemase ($Mg^{2+}$), muconate cycloisomerase ($Mn^{2+}$). In the presence of metal chelating agents (such as EDTA), these enzymes loose their activity completely.

The binding of metal ions in a protein molecule usually involves coordination by 4 or 6 ligands. Depending on the type of metal ion, different ligands are found. For instance magnesium and calcium are usually liganded by oxygen atoms from either a carbonyl group of the protein main chain, a carbonyl group from a glutamine or asparagine side chain or the carboxylate from an aspartic- or glutamic acid side chain. Zinc and copper ions are usually liganded by nitrogen atoms from a histidine side chain or the sulfur atoms from cystein and methionine.

Factors determining the pH dependence of an enzyme

The activity of an enzyme is dependent on the pH value of the aqueous medium. This dependence is caused by the (de)protonation of ionizable groups in the active site of the enzyme on the one hand, and ionizable groups of the substrate, or product (if present) on the other hand. Ionizable groups in proteins involve the side chains of the basic amino acids lysine, arginine and histidine (carrying a positive charge in the protonated form), and the acidic amino acids aspartic acid, glutamic acid, cystein and tyrosine (all carrying a negative charge upon deprotonation). Furthermore, the amino group of the N-terminus and carboxyl group of the C-terminus carry a positive and negative charge respectively. The $pK_a$-values of some amino acids are depicted in Table 1.

TABLE 1.

Ionizable groups of amino acids as occurring in proteins
[Cantor and Schimmel, 1980, Biophysical chemistry, W. H. Freeman, San Fransisco]

| | $pK_a$ |
|---|---|
| Positive charge (base) | |
| N-terminus | 7.5–8.5 |
| Lysine | 10.5 |
| Arginine | 12.5 |
| Histidine | 6.0–7.0 |
| Negative charge (acid) | |
| C-terminus | 3.0–4.0 |
| Aspartic acid | 3.9 |
| Glutamic acid | 4.3 |
| Cystein | 8.3 |
| Tyrosine | 10.1 |

It should be realised that these $pK_a$-values are valid for model compounds and that great variations both within and between different proteins occur, due to the specific environment of the ionizable group. Electrostatic effects are known to play a fundamental role in enzyme function and structures (see J. A. Matthew et al, CRC Critical Reviews in Biochemistry, 18 (1985) 91–197). The presence of a positive charge near an ionizable group will lower its $pK_a$ while a negative charge will cause an increase in $pK_a$. The magnitude of the effect decreases with the distance between the ionizable group and the charge. Moreover, the magnitude of this decrease is dependent upon the dielectric constant of the medium. Especially catalytic residues may reveal $pK_a$-values which deviate from these averages (see for instance Fersht, Enzyme structure and mechanism, 1985, W. H. Freeman, New York).

The pH-dependence of an enzyme catalyzed reaction can be dissected into the pH-dependence of the Michaelis constant $K_m$ and the pH-dependence of the turn-over rate constant $k_{cat}$ (equivalent to $V_{max}$). These parameters represent the binding of the substrate in the groundstate and transition-state respectively. The pH-dependent (de)protonation of amino acid side chains which affect the binding of both substrate forms, or which are otherwise involved in the catalytic event (e.g. proton uptake and release as in general base catalysis), therefore, determine the pH-activity profile of an enzyme.

For instance the protonation of the histidine in the catalytic triad of serine proteases (both the trypsin- and subtilisin family) is responsible for the loss of activity at lower pH-values (<7). In this case, the $pK_a$ of the enzyme activity is directly related to the $pK_a$ of this histidine residue.

As a second example, the two aspartic acid residues in aspartyl proteases, such as pepsin and chymosin, can be mentioned. These groups determine the pH optimum of these proteases. The typical structural arrangement of the aspartic acids causes them to have different $pK_a$-values leading to the bell-shaped pH-activity profile.

It is known that altering the surface charge by extensive chemical modification can lead to significant changes in the pH dependence of catalysis. However in many cases this approach leads to inactivation and/or unwanted structural changes of the enzyme because these methods are rather unspecific. Selective chemical modification of lysines in cytochrome c was shown to have an effect on the redox-potential (D. C. Rees, J. Mol. Biol. 173, 323–326 (1980)). However, these results have been criticized because the bulky chemical reagent used for modification could perturb the structure of the protein.

Using the 3D-structure of a protein to anticipate the possibility of structural perturbation and site-directed mutagenesis, it is possible to modify the charge distribution in a protein in a very selective way.

Fersht and coworkers have shown that it is possible to manipulate the pH-activity profile of subtilisin by site-directed mutagenesis (Thomas et al, Nature, 318, 375–376 (1985); Russell et al, J. Mol. Biol., 193, 803–813 (1987); Russel and Fersht, Nature 328, 496–500 (1987)). Introduction of negatively charged groups at 10–15Å from the active site at the protein surface raises the $pK_a$ value of the active site histidine. Conversely, making the surface more positively charged lowers the $pK_a$ of the acidic groups. Changing either Asp99 at 13 Ångstroms or Glu156 at 15 Ångstroms from the active site to a lysine lowers the $pK_a$ of the active site histidine by 0.6 pH units. Changing both residues simultaneously to give a double mutant with a change of four charge units, lowers the $pK_a$ by 1.0 pH unit. It appears that changes in Coulombic interactions can be cumulative.

Glucose isomerase mutants

WO 89/01520 (Cetus) lists a number of muteins of the xylose isomerase which may be obtained from *Streptomyces rubiginosus* and that may have an increased stability. The selection of possible sites that may be mutated is based on criteria differing from the ones used in the present invention. More than 300 mutants are listed but no data are presented concerning the characteristics and the alterations therein of the mutant enzyme molecules. Methodologies for obtaining enzymes with improved properties Enzymes with improved properties can be developed or found in several ways, for example by classical screening methods, by chemical modification of existing proteins, or by using modern genetic and protein engineering techniques.

Site-directed mutagenesis (SDM) is the most specific way of obtaining modified enzymes, enabling specific substitution of one or more amino acids by any other desired amino acid.

SUMMARY OF THE INVENTION

The subject invention provides new mutant metalloenzymes obtained by expression of genes encoding said enzymes having amino acid sequences which differ in at least one amino acid from the corresponding wildtype metalloenzymes and which exhibit altered catalytic properties. Specifically, the pH-activity profile is altered by changing the overall charge distribution around the active site.

In one of the preferred embodiments of the invention glucose isomerases are mutated.

It is another aspect of the invention to provide a method for selecting sites, in the wildtype enzyme, which can be explored by site-directed mutagenesis in order to modulate the pH-activity profile.

In still another aspect the present invention provides glucose isomerases with a more acidic pH optimum relative to the wildtype glucose isomerase.

BRIEF DESCRIPTION OF THE FIGURES

FIG. 2 shows the alignment of amino acid sequences (SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9) of glucose isomerases from different sources. FIG. 2A shows the amino terminal portion of these sequences; FIG. 2B shows the carboxy terminal region of these sequences. The complete sequence of *Actinoplanes missouriensis* glucose isomerase is given. The amino acid sequence of Ampullariella glucose isomerase differs from that of the published sequences (Saari, J. Bacteriol., 169, (1987) 612) by one residue: Proline 177 in the published sequence was found to be Arginine.

The *Streptomyces thermovulgaris* sequence has only been established up to amino acid 346. Undetermined residues are left blank. A dot indicates the absence of an amino acid residue at this position as compared to any of the other sequences. The different species are indicated by the following symbols:

Amp.: *Actinoplanes missouriensis* DSM 4643
Amp.: Ampullarella species ATCC31351
Svi.: *Streptomyces violaceoruber* LMG 7183
Smu.: *Streptomyces murinus*
Sth.: *Streptomyces thermovulgaris* DSM 40444
Art.: Arthrobacter species
Bsu.: *Bacillus subtilus*
Eco.: *Escherichia coli*
Lxy.: *Lactobacillus xylosus*

The secondary structure assignment was made in the structure of *Actinoplanus missouriensis*. The helices in the barrel are enclosed by solid lines. The $\beta$-strands are in the shaded boxes.

Figure 3:
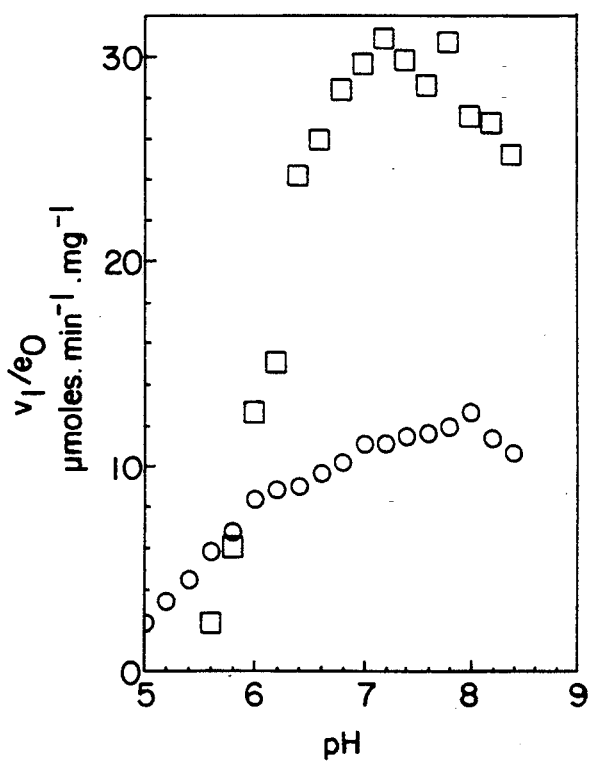

FIG. 3 shows the pH-activity profile of glucose isomerase in the presence of 200 mM xylose and 10 mM magnesium (um squares) and 1 mM manganese (circles).

Figure 4:
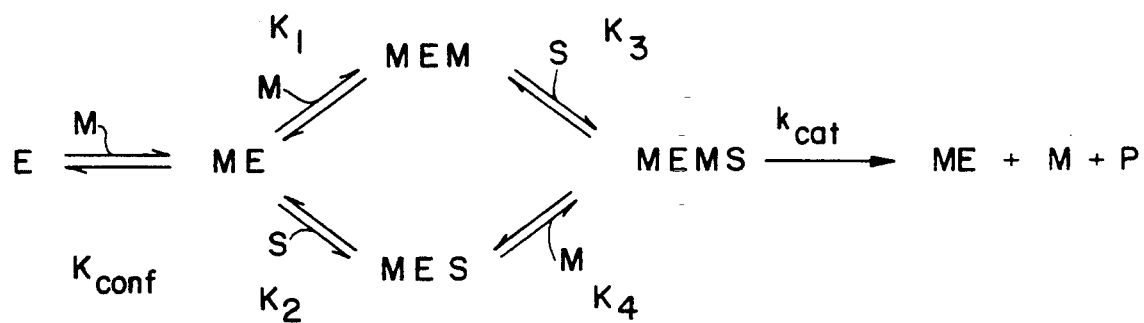

FIG. 4 shows the reaction scheme for the isomerisation catalyzed by glucose isomerase in the presence of metal ions.

E=enzyme, S=substrate, M=metal ion, P=product.

Figure 5C:
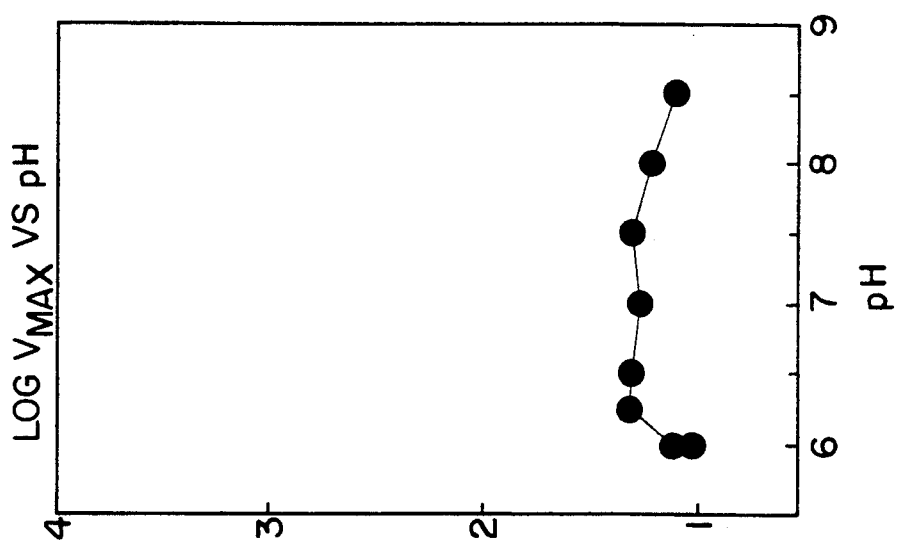
Figure 5B:
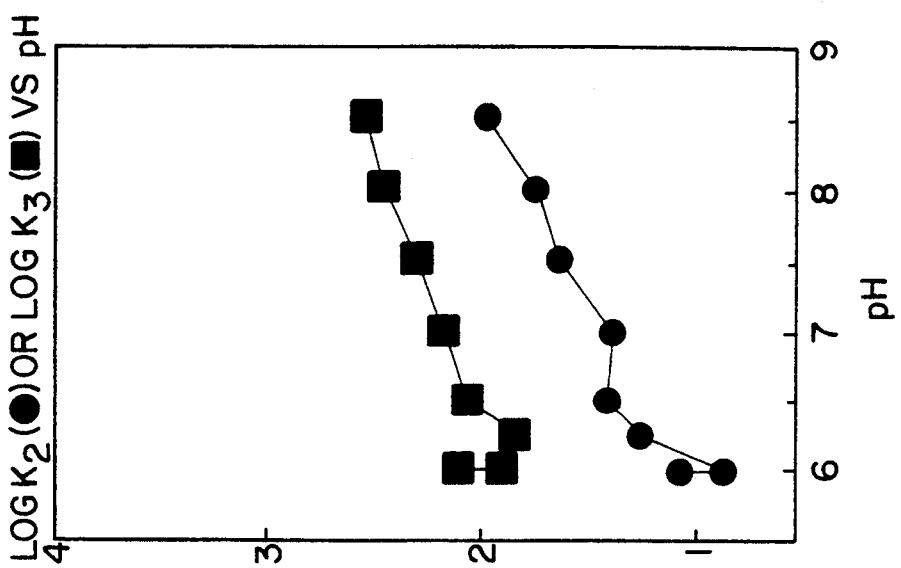
Figure 5A:
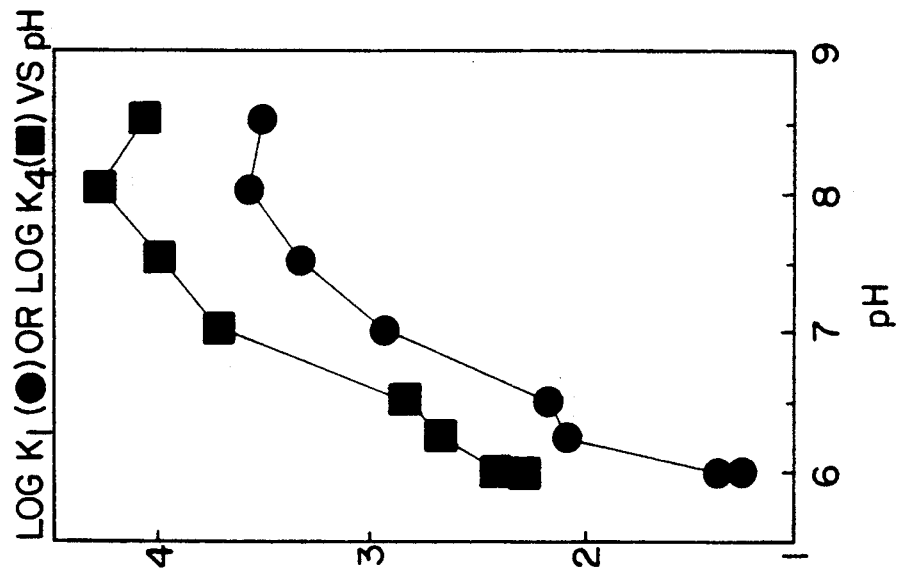

FIG. 5 shows the pH dependence of the reaction of glucose isomerase with xylose and $Mg^{2+}$ as observed with steady-state experiments. $K_1$, $K_2$, $K_3$ and $K_4$ are equilibrium constants explained in the text and in the reaction scheme given in FIG. 4.

Figure 6:
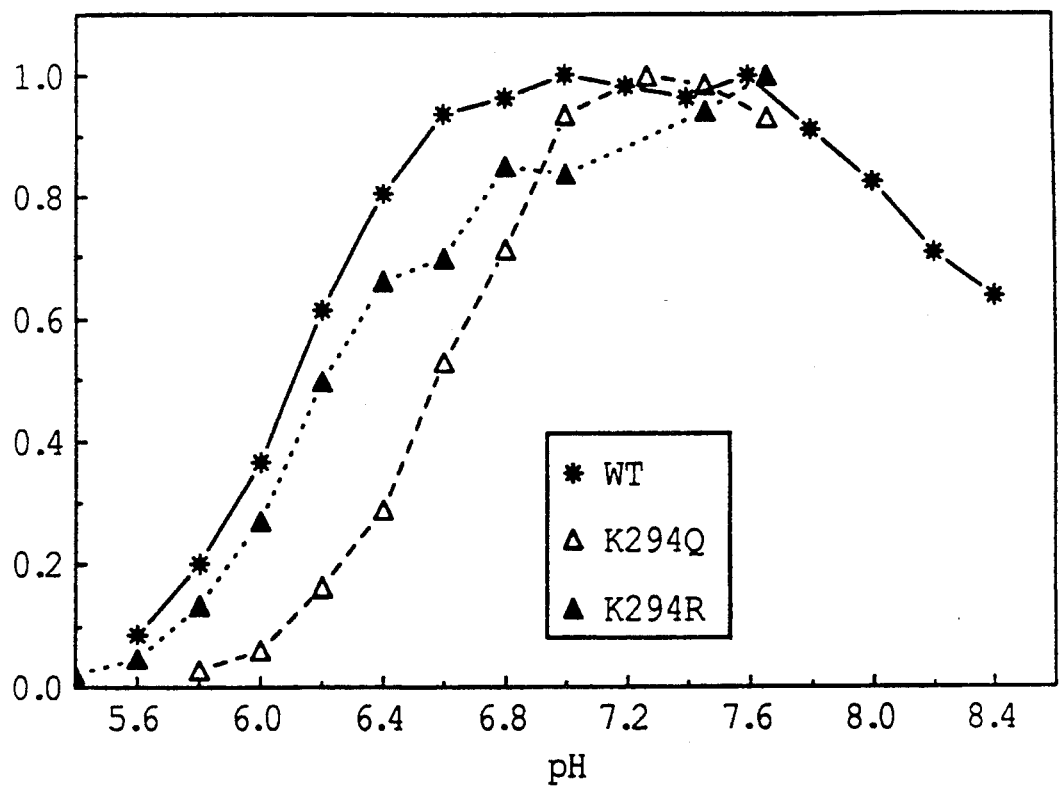

FIG. 6 shows the pH-activity profile for the mutants K294R and K294Q in the presence of 200 mM xylose and 10 mM magnesium.

Figure 7:
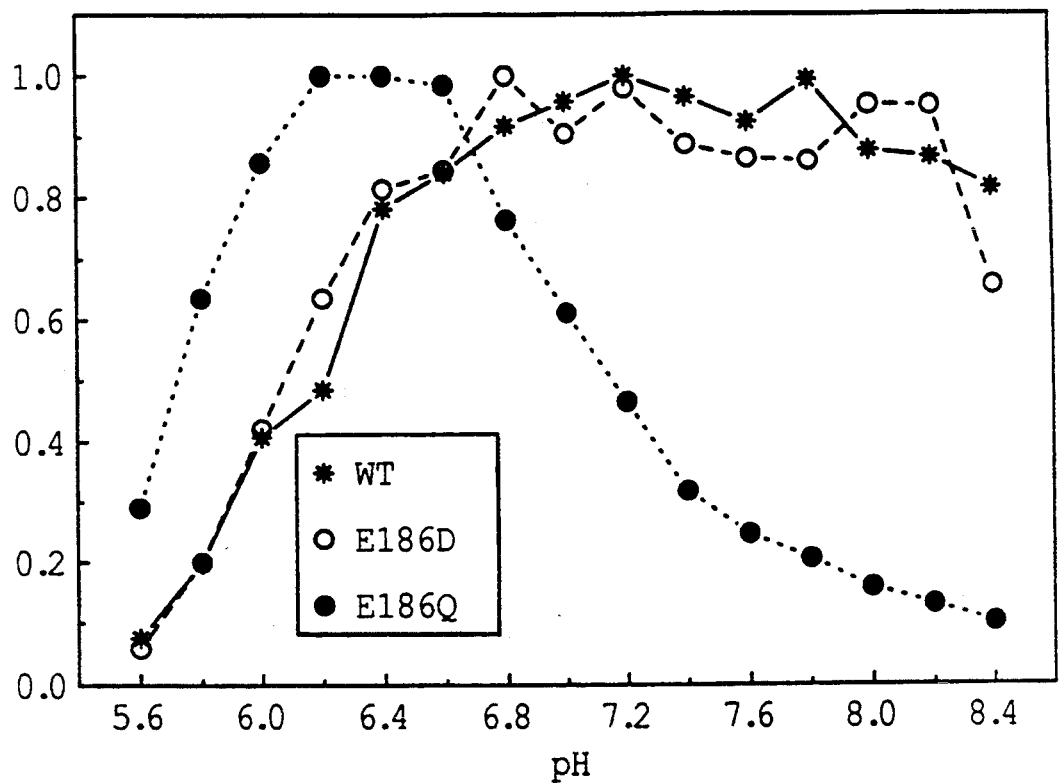

FIG. 7 shows the pH-activity profiles for E186Q and E186D in the presence of 200 mM xylose and 10 mM $Mg^{2+}$.

Figure 8:
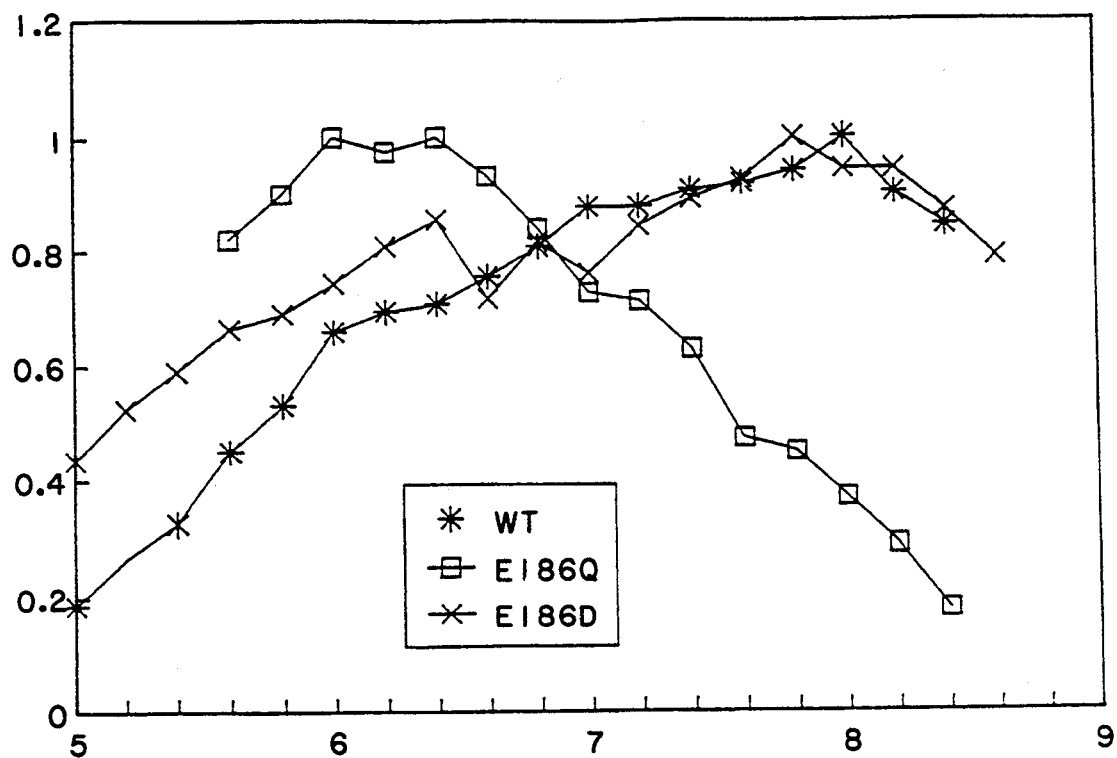

FIG. 8 shows the pH-activity profiles for E186D and E186Q in the presence of 200 mM xylose and 1 mM $Mn^{2+}$.

Figure 9:
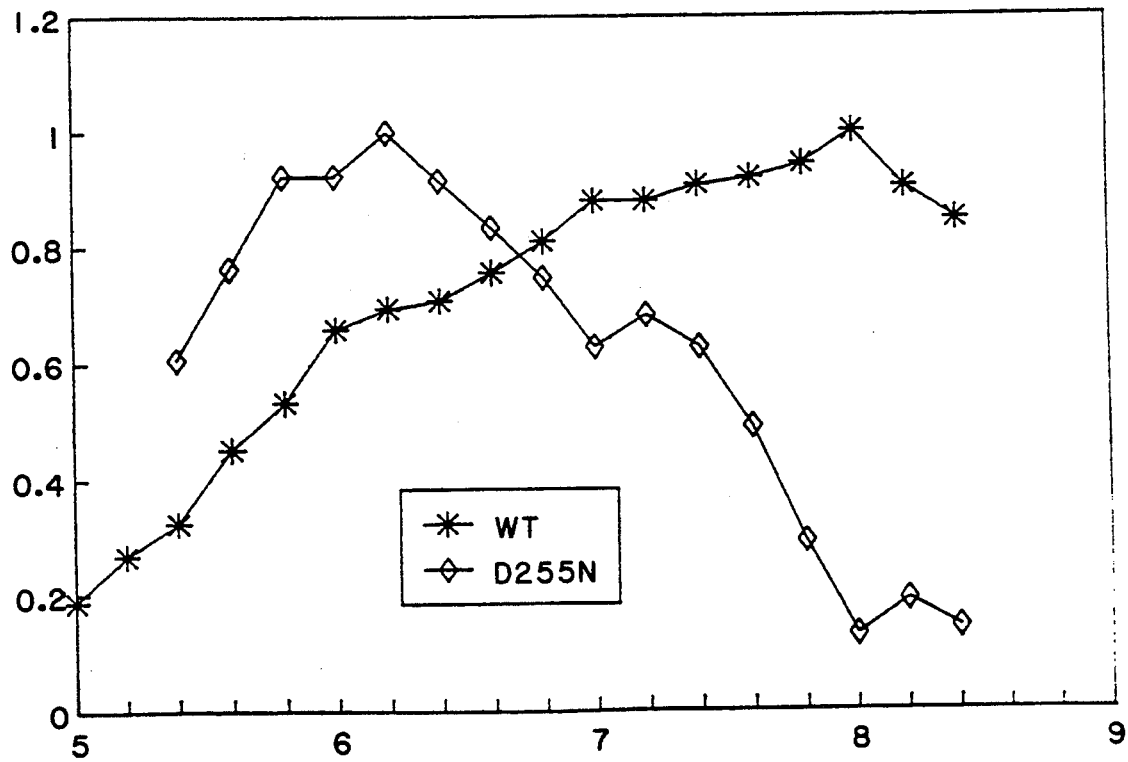
Figure 10:
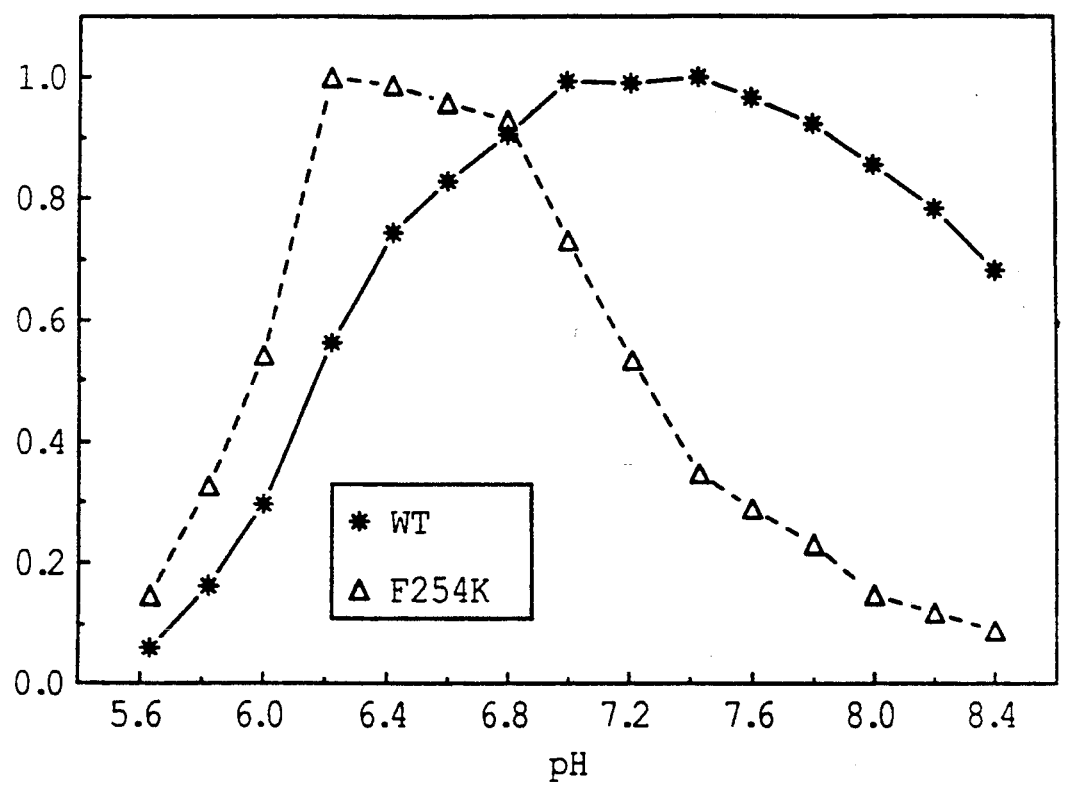
Figure 11:
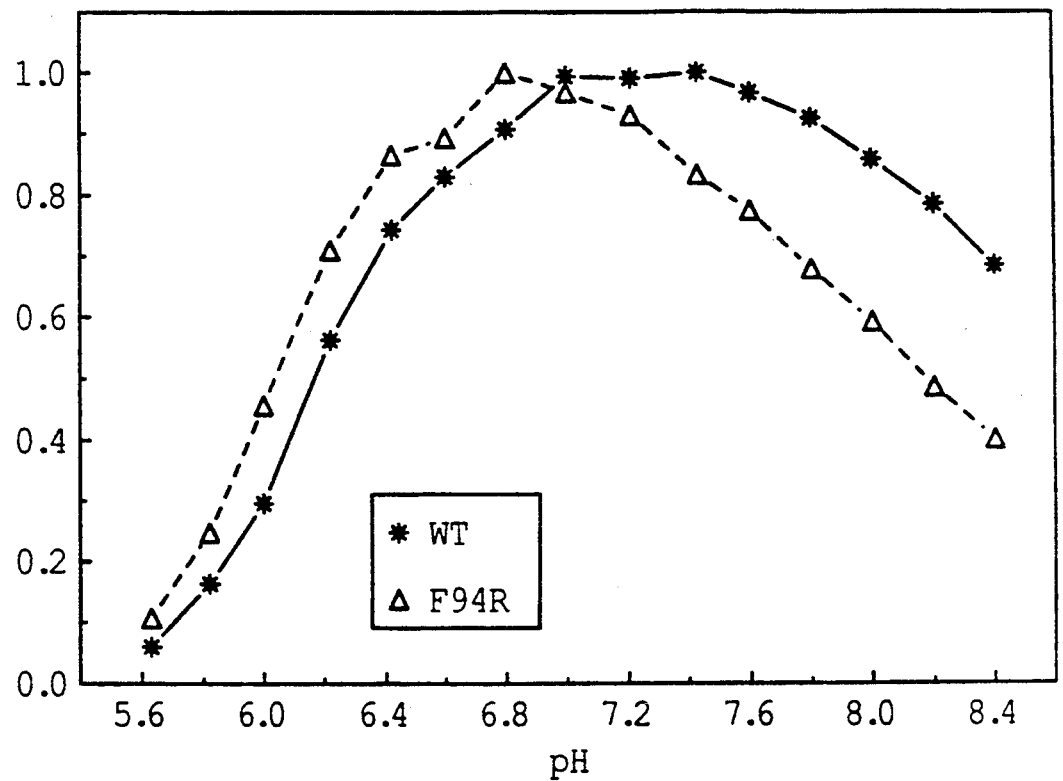
Figure 12:
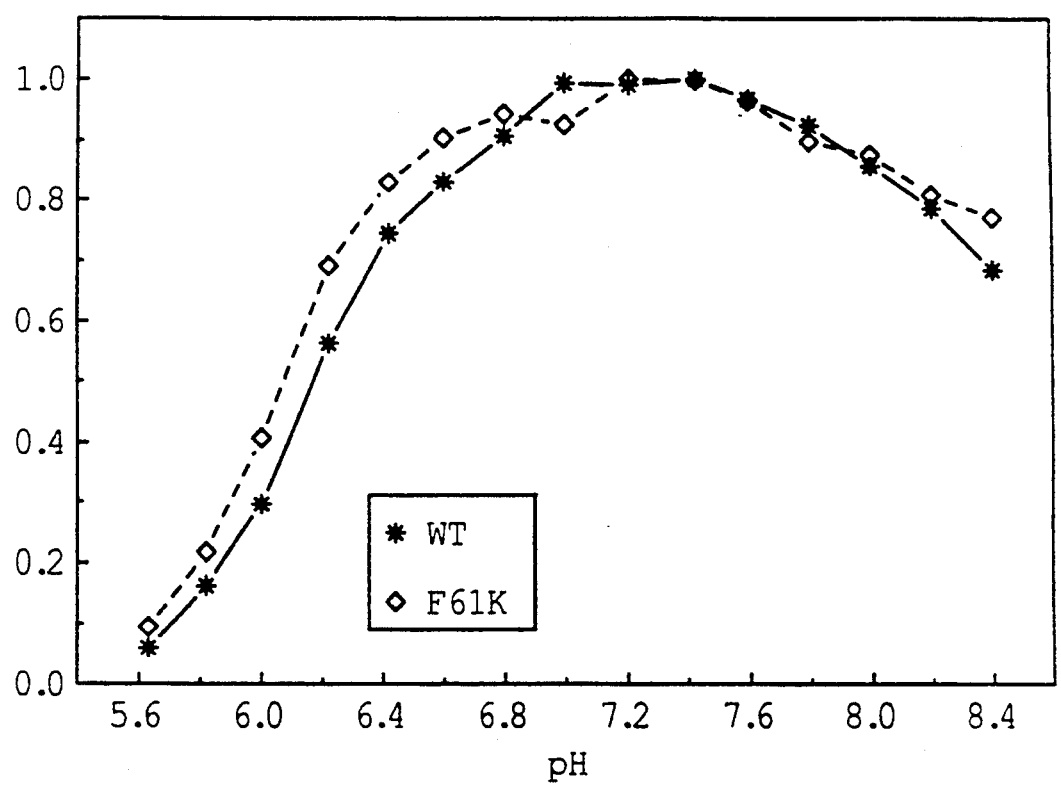
Figure 13:
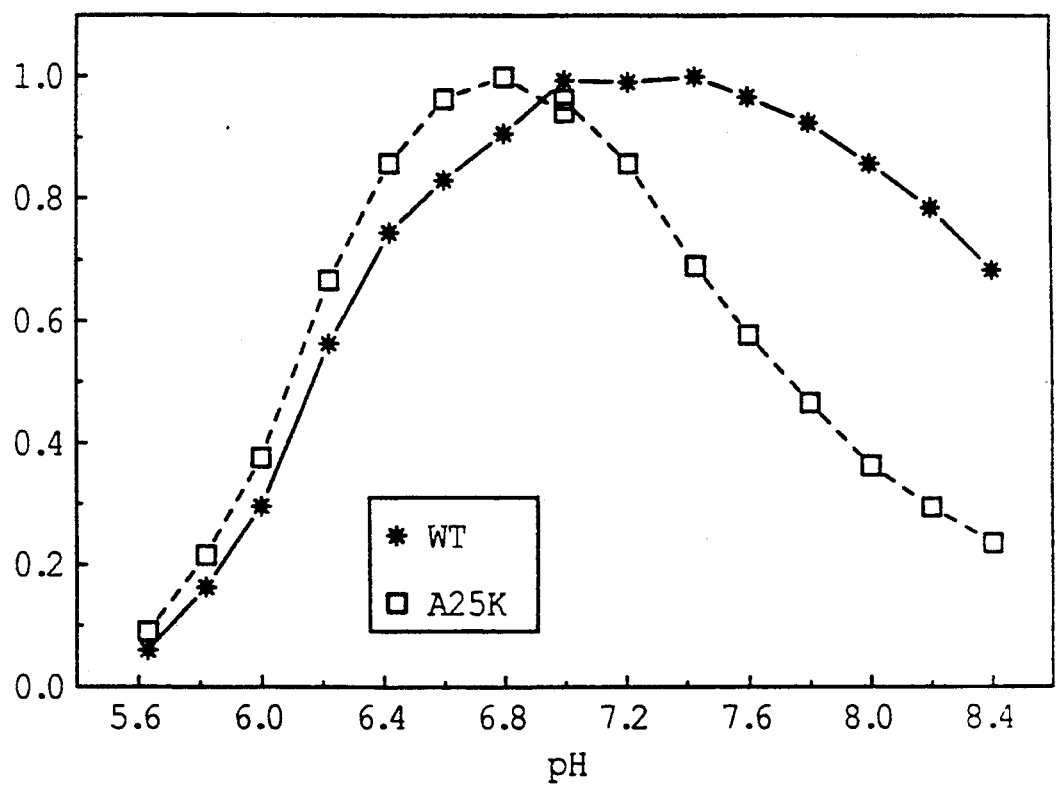
Figure 14:
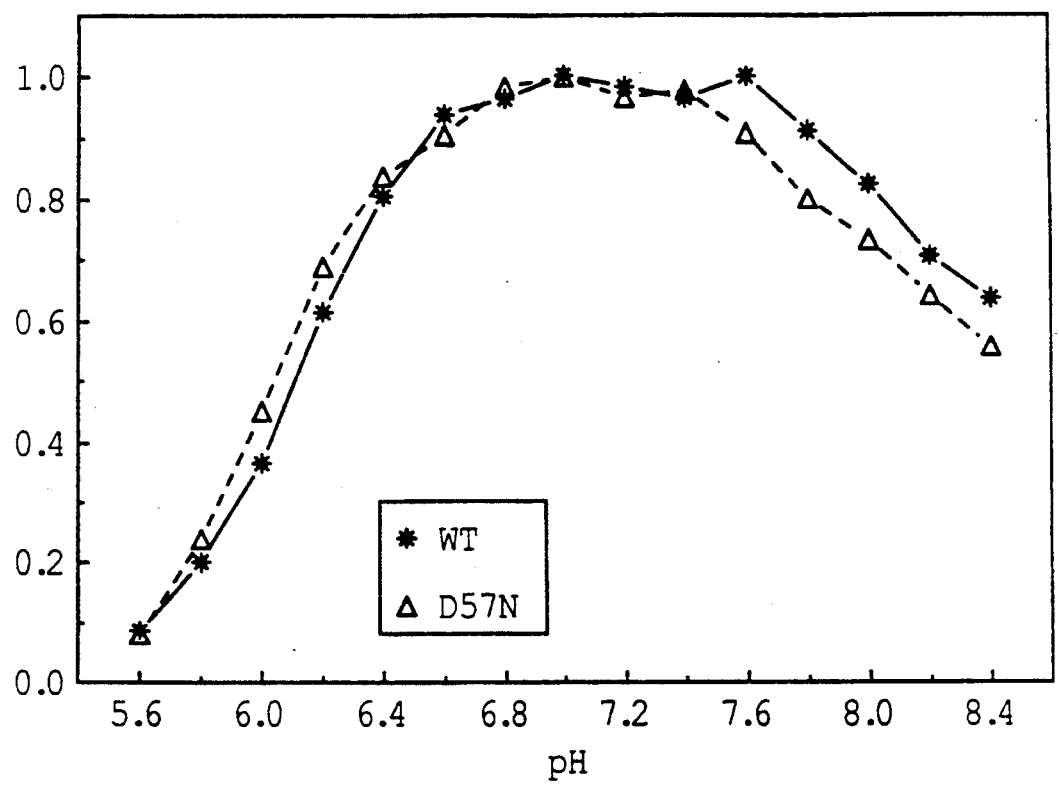
Figure 15:
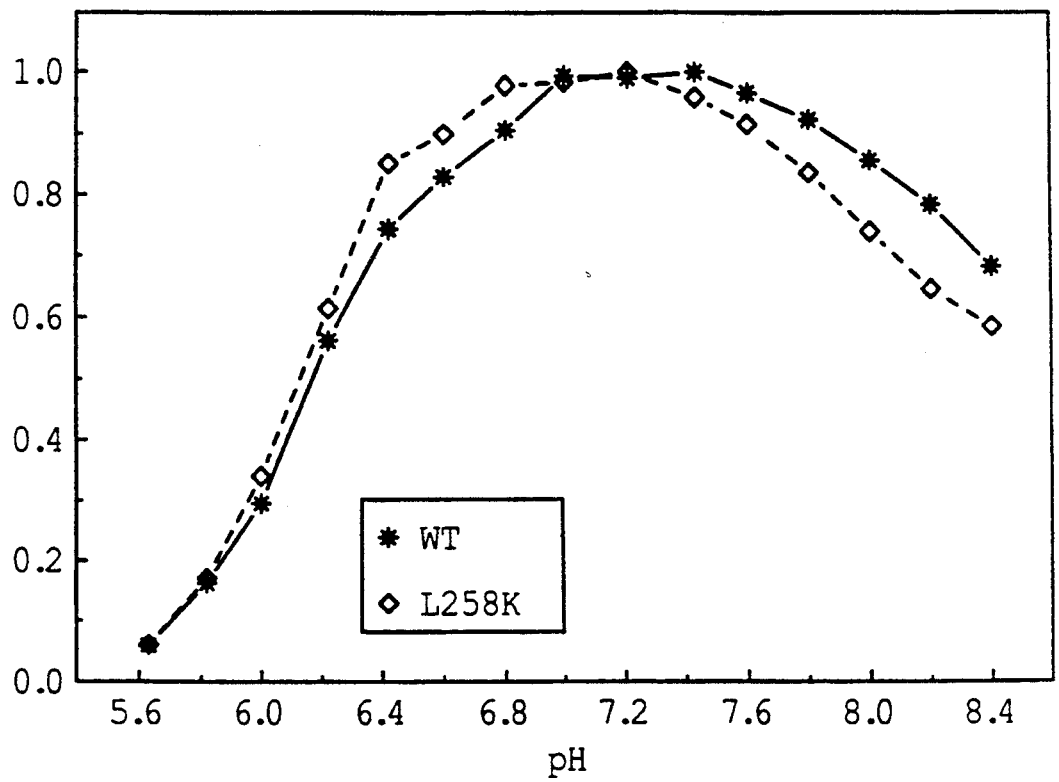
Figure 16:
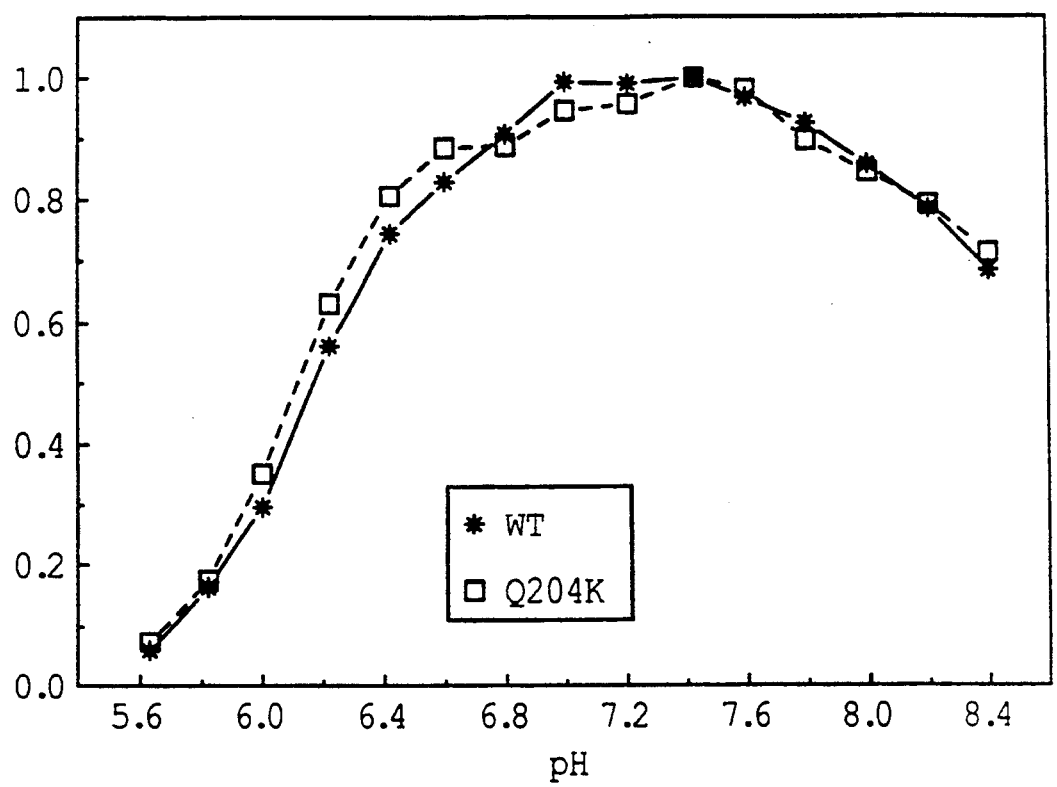
Figure 17:
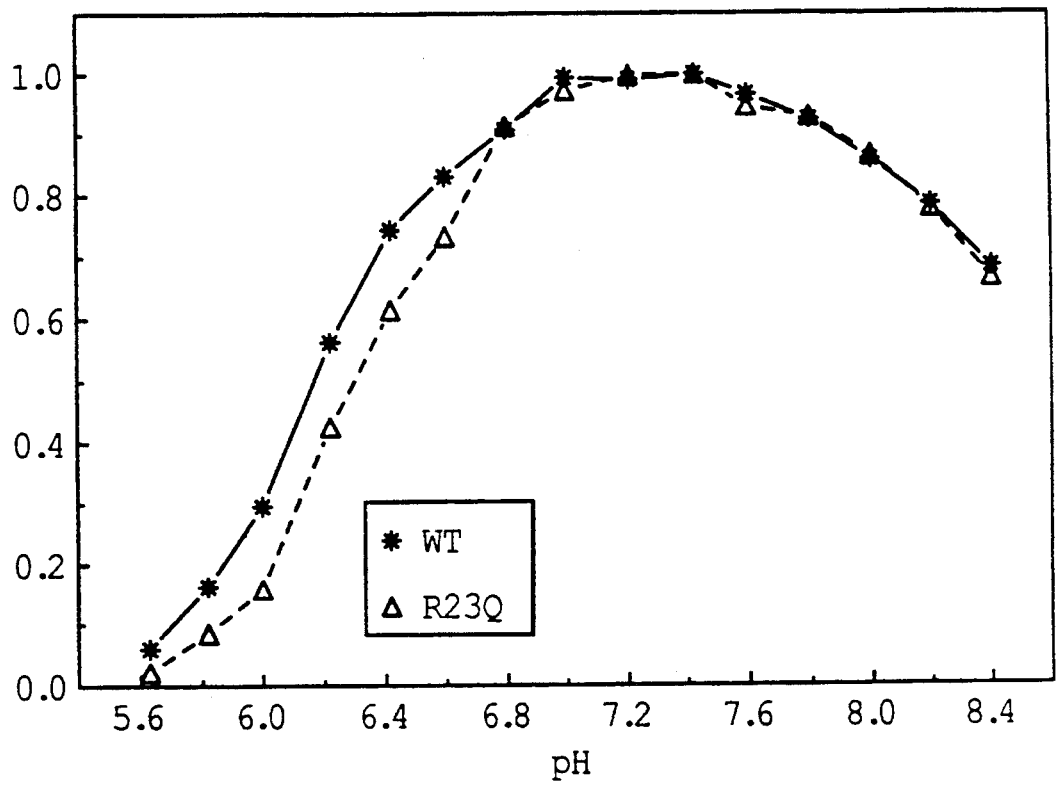
Figure 18:
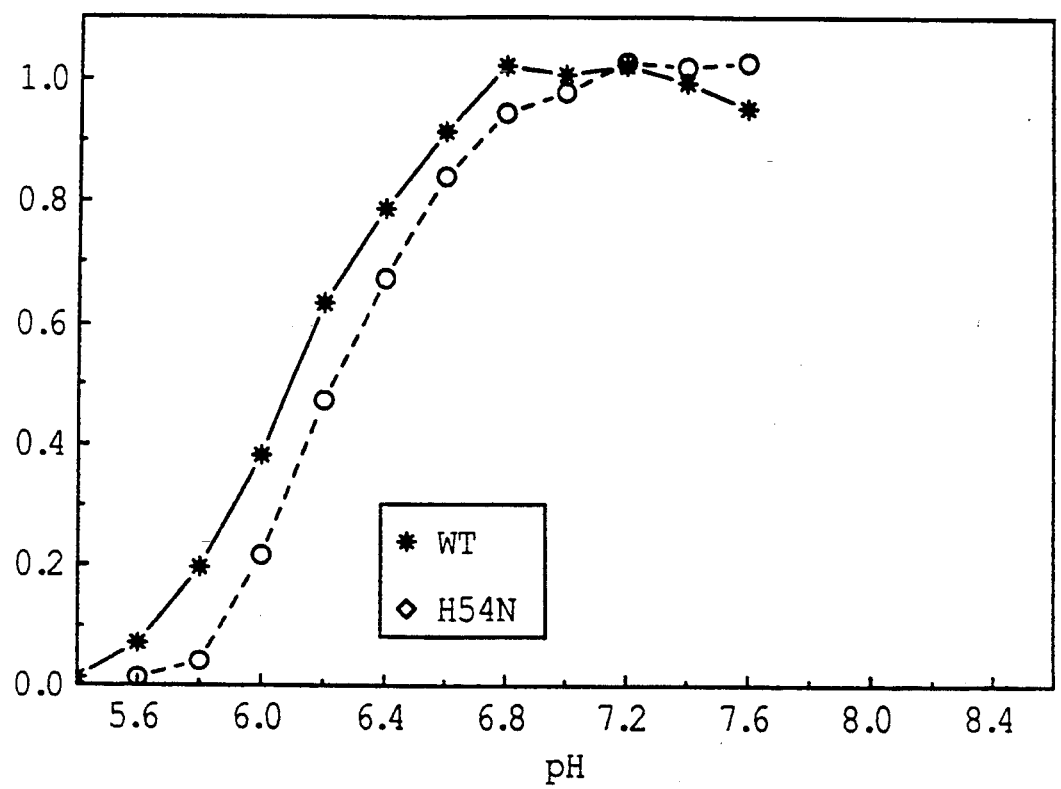
Figure 19:
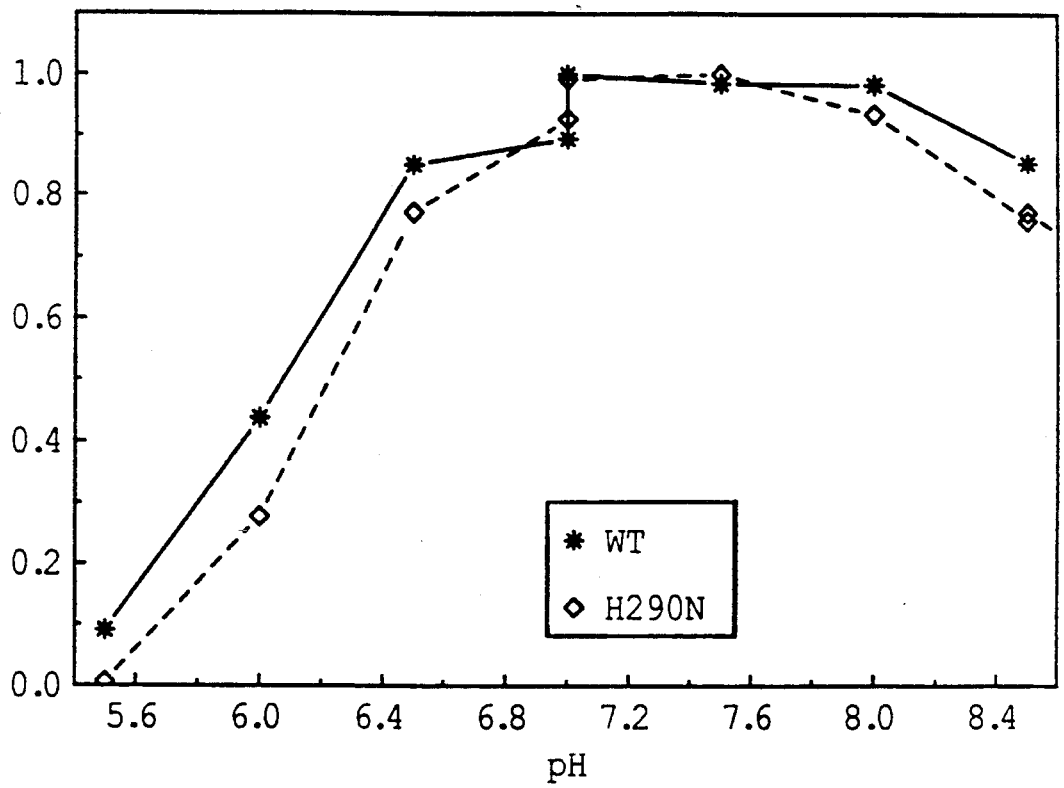

FIG. 9 shows the pH-activity profile of the mutant D255N in the presence of 200 mM xylose and 1 mM manganese.

Figure 20:
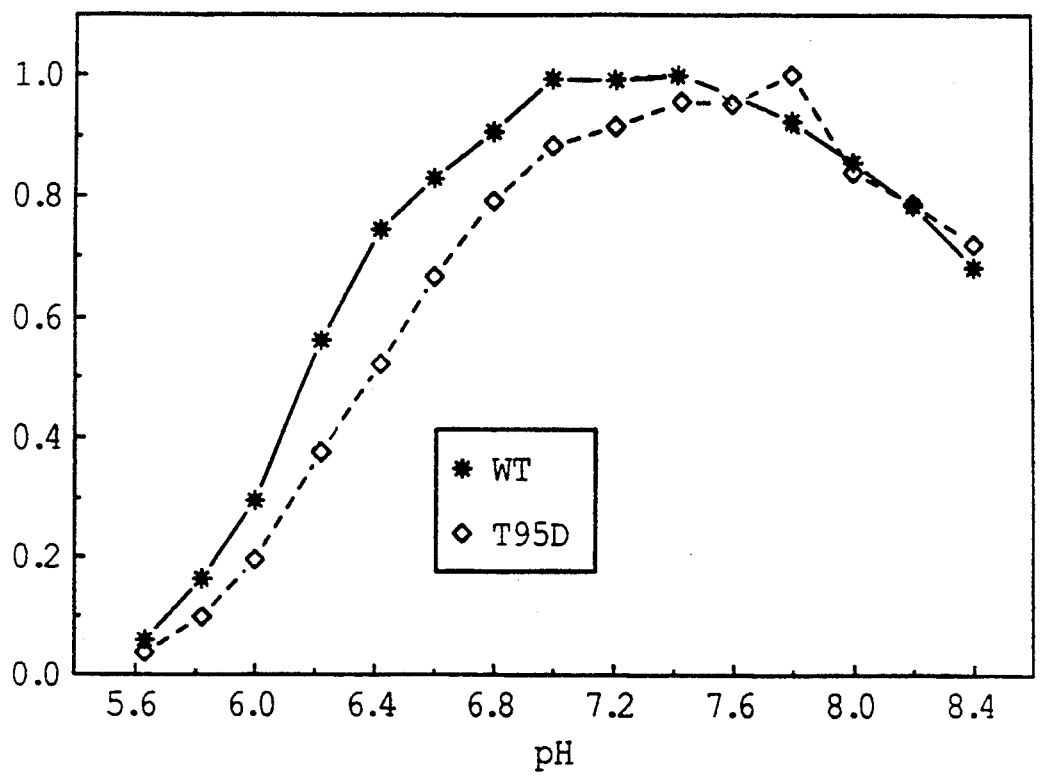

FIGS. 10–20 show the normalized pH-activity profiles for the following mutants:

F254K (FIG. 10), F94R (FIG. 11), F61K (FIG. 12), A25K (FIG. 13), D57N (FIG. 14), L258K (FIG. 15), Q204K (FIG. 16), R23Q (FIG. 17), H54N (FIG. 18), H290N (FIG. 19), T95D (FIG. 20).

Conditions are mentioned in the Figures.

Figure 21:
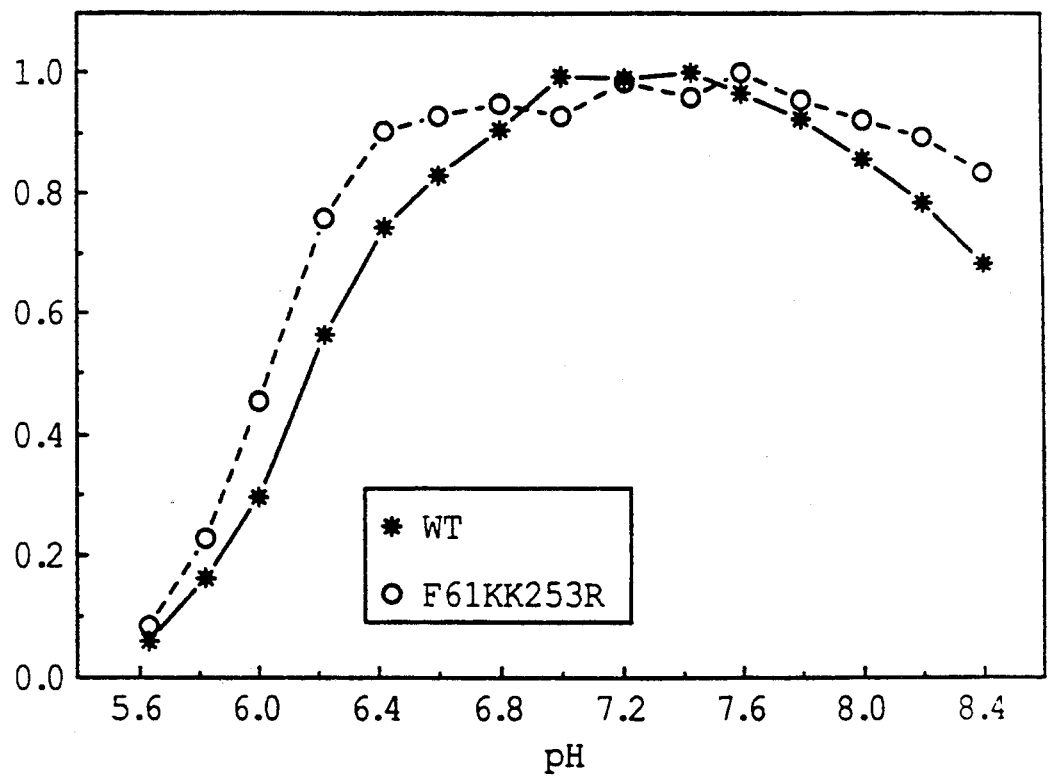

FIG. 21 shows the normalized pH-activity profile for mutant F61KK253R. Conditions are mentioned in the Figure.

DETAILED DESCRIPTION OF THE INVENTION

The present invention describes the modification of enzymes to improve their industrial applicability. The invention makes use of recombinant DNA techniques. Such techniques provide a strong tool for obtaining desired amino acid replacements in the protein of choice. Because of the virtually unlimited amount of possible amino acid replacements it is preferable to use a selective approach. The present approach relies on the well coordinated application of protein crystallography, molecular modelling and computational methods, enzymology and kinetics, molecular biology and protein chemistry techniques. The strategies for the identification of targeted mutations are innovative in the sense that it is recognized that point mutations rarely cause only local perturbations. Mutations generally affect several different properties of the protein at once. Therefore, although the disclosed strategies make use of well established structure-function relationships, they also provide a rational way to avoid or correct unwanted alterations of secondary properties.

Extensive biochemical investigation of the designed mutants results in the identification of mutants with improved properties.

By 'improved properties' as used herein in connection with the present glucose isomerase enzymes we mean enzymes in which the acidic flank of the pH-activity profile shifted towards a more acidic pH optimum relative to the corresponding wildtype enzymes.

It was established that the pH-activity profile of wildtype glucose isomerase reveals a decrease in activity at both acidic pH below 7.0 and at alkaline pH beyond pH 8.0 (Example 1 - FIG. 3). As discussed earlier it would be preferable to use glucose isomerase at lower pH.

Surprisingly, it was found that the drop in activity at the acidic side of the pH-activity profile is caused by the protonation of one or more amino acid side chains, which are directly involved in the coordination of the catalytic metal ion of glucose isomerase. This was deduced from the fact that the apparent association constants for metal binding, as determined by steady-state kinetics, showed a similar pH-dependency (Example 1 - FIG. 5). This can be described by the following model:

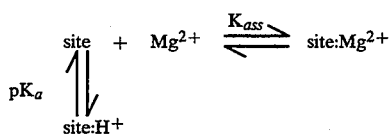

in which "site" refers to the geometrical binding site composed of the different (ionizable) ligands. The enzyme is only active when the site is occupied by an $Mg^{2+}$-ion, which in turn, can only bind to the unprotonated metal binding site ("site") and not the protonated one ("site:$H^+$"). The pH-dependent protonation of the metal binding site is characterized by the $pK_a$, whereas the metal binding to the unprotonated site is characterized by the association constant $K_{ass}$. The apparent association constant for metal binding is a function of the true $K_{ass}$, the $pK_a$ and the pH and can be described as follows:

$$K_{ass}^{apparent} = K_{ass} * (1 + 10^{pKa-pH})^{-1}$$

The rate of the reaction is proportional to the fraction of the enzyme molecules which is complexed with $Mg^{2+}$. This fraction increases at a higher $[Mg^{2+}]*K_{ass}^{apparent}$.

Although the presented model was described after an observation made in glucose isomerase, it is obvious that this model, and the method derived therefrom, can be used for metalloenzymes in general, provided that the inactivation at low pH is due to the dissociation of the metal ions.

The drop in activity observed at alkaline pH is due to a decrease in the maximal velocity ($V_{max}$), reflecting the deprotonation of an amino acid residue that is essential for the catalytic mechanism.

From the model described above, which can be used to explain the decrease in activity at the acidic side of the pH-activity profile, it can be deduced that in order to increase the activity of glucose isomerase at lower pH values, $K_{ass}$ has to be increased and/or the $pK_a$ has to be decreased.

Therefore, in one embodiment of the invention, DNA sequences coding for metalloenzymes such as glucose isomerases are mutated in such a way that the mutant proteins reveal a change in the pH-activity profile as a result of a change in $pK_a$ of amino acid side chains acting as ligands in the metal binding.

Shift of the pH-activity profile of metalloenzymes to lower pH, by changing the $pK_a$ of amino acid side chains In order to shift the $pK_a$'s of metal coordinating ligands to a more acidic pH, residues have to be introduced which increase the overall positive charge around the metal binding site of metalloenzymes. Consequently, the pH dependence of the activity of metalloenzymes, for which the activity at the acidic side of the pH optimum is caused by the $pK_a$ of metal binding, will change accordingly. This charge alteration will stabilize the negative charge of the ionizable groups which are responsible for the pH dependence of the metal binding through long range electrostatic effects.

According to a preferred embodiment the shift of the pH-activity profile of glucose isomerase to a more acidic pH is achieved by increasing the overall positive charge around the active site of glucose isomerase. Around neutral pH a net increase in positive charge can be obtained by:

replacing a negatively charged residue (Asp or Glu) by a neutral one replacing a neutral residue by a positively charged one (Arg or Lys)

replacing a negatively charged residue by a positively one.

For the selection of residues, which are suitable to be mutated, the following criteria can be formulated:

I. Select those positions at which substitution will lead to a net increase in positive charge within a 15 Ångstroms radius around the target residues. The target residues are the ionizable groups which are involved in the coordination of the cation. Eliminate from this collection:

All positions that already contain a positive charge: arginine or lysine.

All positions that cannot harbour an arginine or a lysine because these residues would lead to inadmissible Van der Waals overlap with the backbone atoms of the protein.

All positions at which an arginine or a lysine would need extensive adaptation of additional positions in the direct environment in order to avoid Van der Waals overlap.

All positions at which substitution into arginine or lysine would lead to a buried uncompensated charge in a hydrofobic cluster.

All positions at which residues should not be replaced because they are involved in typical structural arrangements such as: salt bridges, packing of helices, stabilization of helices by keeping a negative charge at the start of a helix, initiation of helices, e.g. prolines at the start of a helix, Phi-psi angles which are outside the allowed region for the residue that is going to be inserted.

II. In a preferred embodiment the following amino acids are also eliminated from the collection:

All residues that are implied in catalysis, cofactor binding (such a metal ions and nucleotides)

All positions that appear to be strictly conserved among homologous enzymes (if available).

III. Subsequently a priority can be attributed to each possible mutation site. This is done by inspection of the structural environment of the residue, the distance to the 'target' residues, the hydrogen bonding pattern in which the residue at said site is involved and the solvent accessibility. In order to avoid masking of the electrostatic interactions by counter-ions, introduction of charges at sites which can not be shielded from the target residues by solvent, are to prefer. So in general, due to the difference in dielectric properties between the protein and the solvent, charges, which cannot be solvated completely due to the fact that they are buried in the interior of the protein or partially buried in clefts on the protein surface, are more likely to cause effects than charges that are completely solvated. Moreover, in the case of glucose isomerase, the conversion of glucose into fructose is performed at low ionic strength, and therefore, shielding by counter-ions is expected to interfere less seriously with the newly designed charge-charge interaction in the novel glucose isomerase described within the embodiment of the invention. Criteria for the assignment of low priority to the above selected sites, when replacing into a positive charge are:

The introduction of a positive charge and/or elimination of a negative charge will affect the integrity of the quaternary structure.

The site is completely solvent accessible so that an introduced charge is expected to be shielded from the target residues by the solvent, which therefore will diminish the effect on pKa of the target residues.

Likewise, increasing the overall negative charge around the metal binding site will shift the $pK_a$'s to more basic pH-values.

Shift of the pH-activity profile of metalloenzymes to lower pH, by increasing $K_{ass}$ for the metal binding In another preferred embodiment of the subject invention the shift of the pH-activity profile to a lower pH is achieved by increasing the $K_{ass}$.

The shift of the pH-activity profile of metalloenzymes to a more acidic pH can be achieved by increasing the association constant for metal binding. The association constant for metal binding can be increased by optimization of the coordination of the metals by the ligands. This may be realised by the introduction of better ligands or by introducing more ligands. Electrostatic interactions can contribute to the association constant for metal binding over much longer distances.

In another preferred embodiment the acidic flank of the pH-activity profile of glucose isomerase is shifted to lower pH by increasing the association constant for metal binding.

Figure 1:
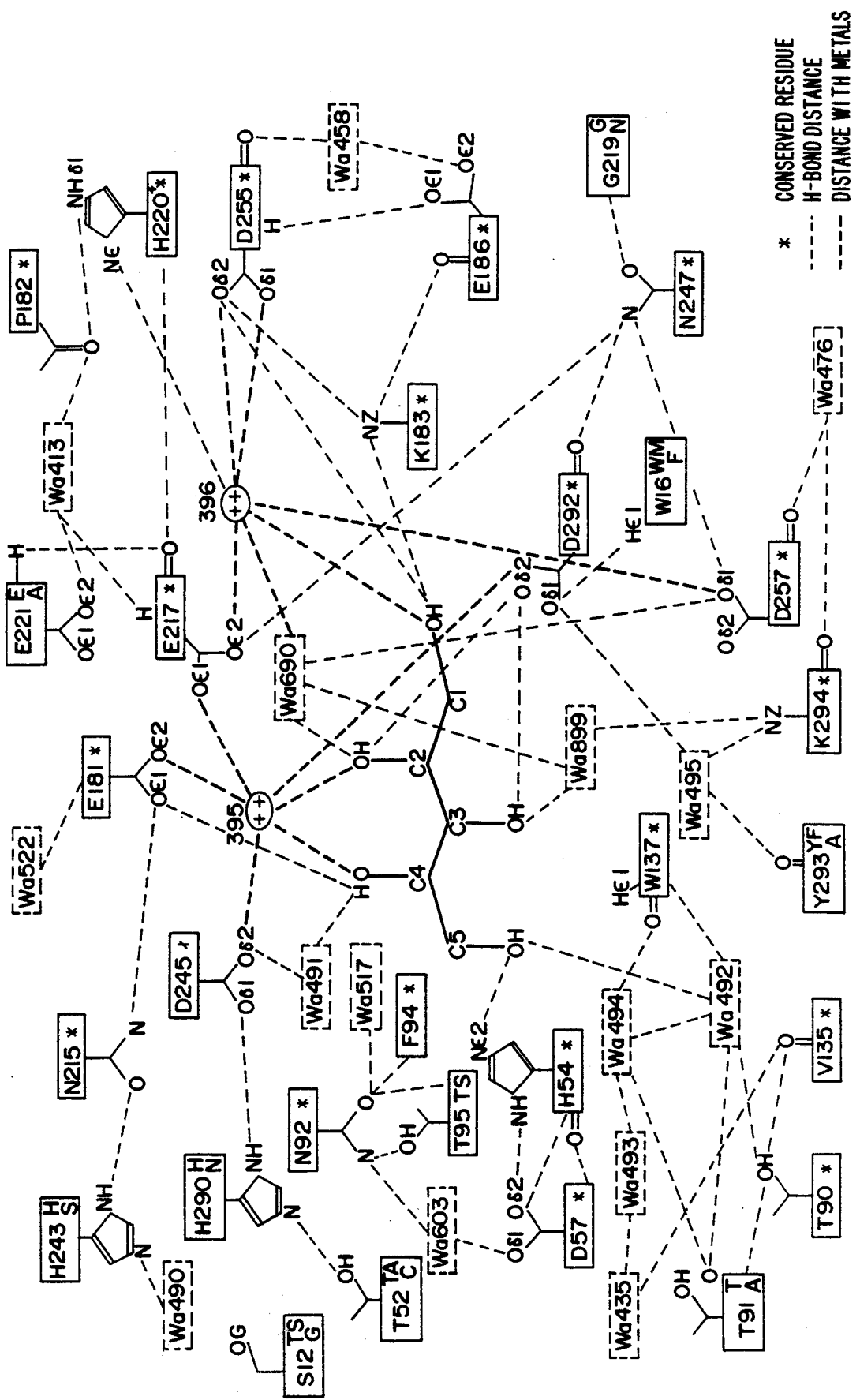
FIG. 1 shows a schematic representation of the active site of glucose isomerase from *Actinoplanus missouriensis*, derived from the three dimensional structure of the glucose isomerase xylitol complex. The inhibitor is shown in full detail in the centre of the figure. For the amino acid residues only those atoms are drawn which are involved in hydrogen bonding. Amino acid residue names are in boxes drawn with solid lines, solvent molecules are in boxes drawn with dashed lines. Metal binding sites are indicated by ovals numbered 395 and 580. Dashed lines indicate electrostatic interactions: the thin dotted lines represent hydrogen bonds, the fat dashed lines the proposed ligation of the metals. Strictly conserved residues are marked by an asterix. For non-conserved residues the substitutions found are indicated.

Glucose isomerase binds two magnesium ions per subunit, resulting in the binding of eight cations per tetramer, thereby increasing the total charge by +16 (see FIG. 1). Both binding sites are located at the C-terminal end of the β-barrel. The 'Down' binding sites is located rather deep in the barrel and, in the xylitol complex, directly binds two oxygens from the inhibitor. The second binding site ('Up') is located near the end of the β-barrel, close to the active site cleft and the subunit interface.

In general, when a positively charged ion binds to a second particle, the association and dissociation rate constants as well as the overall equilibrium affinity constant will depend upon the charge of the second particle. Repulsion occurs when the particle is also positively charged and attraction occurs between opposite charges. For small ions, and in certain cases also proteins, this effect can be quantified by studying the ionic strength dependence of the reaction rate. The rate of association of oppositely charged ions will decrease with increasing ionic strength, the rate of association of the same charges will increase with increasing ionic strength, and when one of the particles is not charged there is no effect of the ionic strength.

The affinity of glucose isomerase for magnesium decreases, with increasing ionic strength which is consistent with an overall negative charge of the glucose isomerase binding site. The binding of the cation may be altered by the introduction of a charged amino acids at the protein surface along the trajectory of the cation upon entrance of the active site. More specifically, this invention relates to the use of electrostatic forces to alter the association rate constant of the cation. Glucose isomerase may be engineered to increase the association rate for the cation by the addition of negative charge (or deletion of positive charge) near the active site channel, or to decrease the association rate for the cation by the addition of positive charge (or deletion of negative charge) near the active site channel. Since the off-rate is not expected to be affected substantially, an altered on-rate will result in an altered overall association constant of the cation. Since the loop regions situated at the C-termini of the β-barrel shape the active site entry, the possible mutation sites are searched in these regions. To avoid possible interference with barrel stability, substitutions in β-strands or α-helices will not be considered. The following rational may be used:

Select all residues in the region between the C-terminal ends of the β-strands and the N-terminal ends of the αhelices.

Reject from further consideration all residues where substitution leads to a decrease of the net positive charge in a sphere of 15 A ngstroms radius around the metal ligands. Introduction of negative charges too close to the metal binding side will shift the $pK_a$ of the metal ligands to a higher pH, which will cancel out the effect of increased $K_{ass}$ at low pH.

Compute for each of the remaining residues its accessible surface area in the context of the protein and using a probe of radius 1.4 Å. Reject residues that are buried in the sense that they have less than 10 Å² accessible surface area.

STRUCTURAL INFORMATION

Information on the 3D structure of the enzyme (or enzyme:substrate or enzyme:inhibitor complex) is of great importance to be able to make predictions as to the mutations which can be introduced.

Structural data have been reported for glucose isomerase of *Streptomyces rubiginosus* (Carrell et al, J. Biol. Chem. 259 (1984) 3230-3236); Carrell et al. Proc. Natl. Acad. Sci USA 86, (1989) 440-4444) *Streptomyces olivochromogenus* (Farber et al, Protein Eng. 1, (1987) 467-475; Farber et al. Biochemistry 28 (1987) 7289-7297), *Arthrobacter* (Hendrick et al., J. Mol. Biol. 208 (1989) 127-157) and *Streptomyces albus* (Dauter et al FEBS Lett. 247, 1-8).

Although not all amino acid sequence data are available for these enzymes the 3D-structural homology with *Actinoplanes missouriensis* glucose isomerase is striking (see F. Rey et .al., Proteins 4 (1988) 165-172). To show the general applicability of the method disclosed in this specification the genes for glucose isomerase originating from various species have been cloned and sequenced. The amino acid sequences of glucose isomerases as deduced from the genes of *Streptomyces violaceoruber, Streptomyces murinus,* Arthrobacter spec. and *Streptomyces thermovulgaris* are shown to be homologous. Published amino acid sequences for the glucose isomerases of *Ampullariella* sp. (Saari, ibid.) and *Streptomyces violaceoniger* (Nucl. Acids Res. 16 (1988) 9337), deduced from the nucleotide sequences of the respective genes, display a close homology to *Actinoplanes missouriensis* glucose isomerase. In addition, WO 89/01520 discloses that the amino acid sequence of *Streptomyces rubiginosus* glucose isomerase is homologous to *Ampullariella* sp. glucose isomerase.

Despite the absence of 3D structural data for most glucose isomerases, it can be concluded that all glucose isomerases from Actinomycetales have a similar tetrameric organisation.

In general, it can be assumed that where the overall homology is greater than 65%, preferably greater than 74% (minimal homology between *Actinoplanes missouriensis* and Streptomyces glucose isomerase, according to Amore and Hollenberg, Nucl. Acids Res. 17, 7515 (1989)), and more preferably greater than 85% and where the 3D structure is similar, amino acid replacements will lead to similar changes in pH optimum. Specifically one expects the glucose isomerases from species belonging to the order of the *Actinomycetales* to have such a high degree of similarity that the alteration of pH optimum due to amino acid replacements at the selected sites are similar. *Actinoplanes missouriensis* is the preferred source of glucose isomerase to mutate.

FIG. 1 gives a schematic presentation of the active site of the glucose isomerase from *Actinoplanes missouriensis.*

FIG. 2 shows the aligned amino acid sequences of various glucose isomerases.

In the present specification both the three letter and the one letter code for amino acids is used (see e.g. Stryer, L. Biochemistry, p.13, 2nd ed, W. H. Freeman and Comp., N.Y., 1981).

EXPERIMENTAL

Cloning and expression of the D-glucose isomerase gene

D-glucose isomerase (GI) is synonymously used for D-xylose isomerase ((D-xylose) ketol-isomerase, EC 5.3.1.5), an enzyme that converts D-xylose into D-xylulose. The D-glucose isomerase from *Actinoplanes missouriensis* produced by engineered *E. coli* strains is designated as EcoAmi (DSM) GI. To distinguish the *Actinoplanes missouriensis* gene coding for GI from the analogous *E. coli* xylA gene, the former will be designated as GI.

Methods for manipulation of DNA molecules are described in Maniatis et al. (1982, Cold Sprong Harbor Laboratory) and Ausubel et al. (1987, Current Protocols in Molecular Biology, John Wiley & Sons Inc. New York). Cloning and DNA sequence determination of the glucose isomerase gene from *Actinoplanes missouriensis* DSM 43046 is described in EP-A-0351029. The derived amino acid sequence of GI is numbered and compared with other glucose isomerases in FIG. 2. In the following, the numbering of amino acids refers to FIG. 2.

Wildtype and mutant GI enzymes were produced in *E. coli* strain K514 grown as described in EP-A-0351029.

Assay of the enzymatic activity of the expression product

The enzymatic activity of glucose isomerase was assayed as described below (1 unit of enzymatic activity produces 1.0 micromole of product -D-xylulose or D-fructose-per minute; therefore, specific activity -spa- is expressed as units per mg of GI enzymes).

GI activity can be assayed directly by measuring the increase in absorbance at 278 nm of xylulose produced at 35° C. by isomerisation of xylose by glucose isomerases. This assay was performed in 50 mM triethanolamine buffer, pH 7.5, containing 10 mM $MgSO_4$, in the presence of 0.1 M xylose. Glucose isomerase final concentration in the assay was $\pm 0.01$ mg/ml, and precisely determined, prior to dilution in the enzymatic assay mixture, by absorption spectroscopy using an extinction coefficient of 1.08 at 278 nm for a solution of enzyme of 1.0 mg/ml.

The specific activity was determined in the *D-Sorbitol Dehydrogenase Coupled Assay*, enzymatic determination of D-xylulose was performed at 35° C. as previously described (Kersters-Hilderson et al., Enzyme Microb. Technol. 9 (1987) 145) in 50 mM triethanolamine, pH 7.5, 10 mM $MgSO_4$, and 0.1M xylose, in the presence of $\pm 2 \times 10^{-8}$M D-sorbitol dehydrogenase (L-iditol: NAD oxidoreductase, EC 1.1.14), and 0.15 nM NADH, except that the incubation buffer also included 1 mM ethylenebis(oxyethylenenitrilo)tetraacetic acid (EGTA). Glucose isomerase final concentration in this assay was $\pm 2.5 \times 10^{-3}$ mg/ml, and precisely determined as described above.

With glucose as a substrate GI activity can be assayed by the measurement of D-fructose produced during the isomerization reaction using the cysteine-carbazole method (CCM) which is based on the reaction of keto-sugars with carbazole in acids to yield a purple product (Dische and Borenfreund, J. Biol. Chem. 192 (1951) 583).

EXAMPLE 1

The pH dependence of glucose isomerase activity

In order to determine the pH-activity profile of wildtype and mutant glucose isomerase, the activity was measured as a function of pH (5.2–8.0) in the presence of 10 mM $MgSO_4$ and 200 mM xylose (using the direct assay method). For mutants with very low activity the coupled sorbitol dehydrogenase assay system was used between pH 5.8 and 8.4. Care was taken that the sorbitol dehydrogenase reaction did not become rate limiting at extreme pH values.

The pH-activity profile of glucose isomerase (i.e. the recombinant wildtype enzyme from *Actinoplanus missouriensis*) in the presence of 200 mM xylose and different activating cations is shown in FIG. 3. It reveals a decrease in activity at both acidic pH below 7.0 and at alkaline pH beyond 8.0.

The appropriate steady-state kinetic mechanism for glucose isomerase involves the rapid formation of an enzyme-metal-sugar complex which is converted to the product in a rate limiting step (so called rapid equilibrium, random ordered mechanism—see FIG. 4). Equilibrium and transient kinetic fluorescence measurements (stopped flow) indicate the presence of two metal ion binding sites. In the stopped flow experiment the metal ions bind consecutively. The high affinity metal plays a role in maintaining an active conformation and is therefore called the 'conformational' site. The second metal binding site accommodates the activating cation, therefore this site is usually indicated as the 'catalytic' site. The reaction scheme which is shown in FIG. 4 appears to be adequate to analyze and compare steady-state and stopped flow experiments. In principle steady-state results do not distinguish between the two metal binding sites, but it is assumed that the main effect comes from the catalytic metal binding.

Analysis of the initial rate (v) of xylose conversion as a function of the xylose and magnesium concentrations allows to determine four parameters: the maximal velocity, the equilibrium constants for magnesium binding to the free enzyme ($K_1$), the enzyme-sugar complex ($K_4$), and the equilibrium constants of xylose binding to the free enzyme ($K_2$) and the enzyme-magnesium complex ($K_3$).

$$\frac{V_{max}}{v} = 1 + \frac{1}{K_3 * [S]} + \frac{1}{K_4 * [M]} + \frac{1}{K_3 * K_1 * [S] * [M]}$$

where [M] and [S] represent the concentration of the metal ion and xylose respectively.

By systematic variation of the magnesium ion and the xylose concentrations it was possible to obtain values for the maximal velocity and for all four equilibrium constants. FIG. 5 shows the pH dependance of these parameters.

Comparison of the results of FIGS. 3 and 5, shows that the acidic side of the pH profile is completely determined by the metal ion binding.

The data of FIG. 5 are not sufficiently accurate to calculate the number of ionizations involved. The slope of the plots of log$K_{1,4}$ vs pH (slope>1) indicates however, that more than one ionization may be involved. The similarity in pH dependence of $K_1$ and $K_4$ indicates that the same ionizing groups are important for both these processes (involving the same site).

EXAMPLE 2

Selection of amino acid residues in glucose isomerase of which substitution will alter the p$K_a$ values of the metal binding, ionizable amino acids.

In the case of glucose isomerase, the criteria for the selection of possible positions for substitution, as outlined in the detailed description of this invention, were applied using the aligned sequences from different sources (FIG. 2) and the highly refined structure of *Actinoplanes missouriensis* glucose isomerase in complex with the inhibitor xylitol (see FIG. 1 and "Structural Information" in the "Detailed description of the invention"). The highly refined structure with a resolution of 2.2 Ångstroms reveals the position of the inhibitor and two metal binding sites. A schematic representation of the active site of glucose isomerase of *Actinoplanes missouriensis* is given in FIG. 1.

From the glucose isomerase structure complexed with cobalt and xylitol those residues were selected where substitution into a more positively charged amino acid residue leads to a net increase in positive charge within a 15 Ångstrom radius around the target ionizable groups. In the case of glucose isomerase the targets are the ionizable groups that are involved in the coordination of the metal ions required for activity. These target ionizable groups imply the carboxyl groups of Glu181, Glu217, Asp245, Asp255, Asp292 and the NE of His220.

After application of criterion I, 80 possible mutation sites were retained. These sites are summarized below:
Ala5, Phe11, Leu15, Trp20, Gln21, Ala25, Phe26, Asp28, Ala29, Gly47, Tyr49, Thr52, Phe53, His54, Asp56, Asp57, Phe61, Ile85, Met88, Phe94, Thr95, Phe104, Gln122, Thr133, Leu134, Val135, Ala143, Tyr145, Tyr158, Asn163, Ser169, Glu181, Asn185, Glu186, Glu189, Ile191, Pro194, His198, Gln204, Leu211, Phe212, Asn215, Glu217, Thr218, His220, Gly221, Gln222, Ser224, Asn225, Leu226, Phe228, Thr229, Gly231, Leu236, His238, His243, Asp245, Asn247, His250, Phe254, Asp255, Gln256, Asp257, Leu258, Val259, Phe260, His262, Leu271, Tyr285, Asp286, His290, Asp292, Tyr293, Thr298, Glu299, Trp305, Ala310, Met314, Val380, Asn383.

After discarding the catalytic residues and the strictly conserved residues (criterion II) the following 62 residues are left:
Ala5, Leu15, Gln21, Ala25, Phe26, Asp28, Ala29, Gly47, Tyr49, Thr52, Asp56, Phe61, Ile85, Met88, Thr95, Phe104, Gln122, Thr133, Leu134, Ala143, Tyr145, Tyr158, Asn163, Ser169, Asn185, Gly189, Ile191, Pro194, His198, Gln204, Leu211, Phe212, Thr218, Gln222, Ser224, Asn225, Leu226, Phe228, Thr229, Gly231, Leu236, His238, His243, His250, Phe254, Gln256, Asp257, Leu258, Val259, His262, Leu271, Tyr285, Asp286, His290, Tyr293, Thr298, Glu299, Trp305, Ala310, Met314, Val380, Asn383.

Subsequently a priority was attributed to each of these 62 possible mutation sites according to criterion III.

The following 24 sites were attributed as having high priority for mutagenesis:
Ala25, Gly47, Tyr49, Thr52, Phe61, Ile85, Thr95, Gln122, Thr133, Tyr145, Tyr158, Gly189, Ile191, Gln204, Thr218, Gln222, Leu226, Thr229, Gly231, Leu236, Gln256, Leu258, Tyr293 and Val380.

Mutation of either one or several of the 80 selected amino acid residues into positively charged residues will result in a decrease of the p$K_a$ of metal binding of glucose isomerase. This may result in a corresponding shift of the pH-activity profile towards lower pH.

Correspondingly, mutation of either one or several of the 80 selected amino acid residues into negatively charged residues will result in an increase of the p$K_a$ of metal binding of glucose isomerase. This may result in a corresponding shift of the pH-activity profile towards higher pH.

EXAMPLE 3

The effect of mutating Lys 294 on the pH-activity profile

At position 294 in glucose isomerase a positive charge is located about 8 Ångstroms from the highest occupied metal binding site in the glucose isomerase-xylitol complex (395 in FIG. 1). A mutation at this site was made, replacing the lysine for an arginine. This mutation conserves the positive charge at position 294. Consistent with this conservation of the positive charge is the observation that the pH-activity profile of this mutant is similar to that of the wildtype enzyme.

However, when at position 294 the positive charge is removed by replacing lysine 294 by a glutamine we observed a shift of the pH-activity profile towards the alkaline site by approximately 0.5 pH units. The pH-activity profiles for K294R and K294Q are shown in FIG. 6.

This example illustrates that it is possible to manipulate the $pK_a$ of one or more functional groups, in the active site of glucose isomerase, by changing the net charge of the protein around the active site.

EXAMPLE 4

The effect of mutating Glu186 and replacing magnesium ions by manganese ions on the pH-activity profile In the mutant E186Q a negative charge is replaced by a neutral one which gives rise to a net increase in positive charge within a 15 Ångstroms radius around the metal ligands. The pH-activity profile of the E186Q mutant in the presence of magnesium is shown in FIG. 7. The alkaline flank of the pH profile is shifted significantly toward lower pH. In the presence of manganese instead of magnesium the pH-activity profile of E186Q is shifted to a lower pH and at its optimum pH its activity is higher than for the wildtype (FIG. 8).

For applications where metal ions other than magnesium can be used the combination E186Q with manganese at low pH is an interesting option.

We also performed the mutation E186D which is conservative with respect to charge. The pH-activity profile of this mutant is shown in FIGS. 7 and 8. The pH dependence of the activity for the E186D mutant is not significantly different from that of the wildtype enzyme. Removal of the negative charge at position 186 did shift the pH activity profile to a more acidic pH. This example emphasizes that the rationale of the mutation E186Q holds.

EXAMPLE 5

The effect of replacing Asp255 on the pH-activity profile

Substitution of the negatively charged aspartic acid at position 255, which is in fact a metal binding ligand in glucose isomerase, by a neutral asparagine, gives rise to a shift of the pH-activity profile towards lower pH in the presence of manganese. The pH optimum shifts about 2 pH units towards more acidic pH.

The pH-activity profile is given in FIG. 9.

EXAMPLE 6

Glucose isomerases with an altered pH-activity profile

Mutants of glucose isomerase which were created according to the methods as outlined in the detailed description of the invention, were tested for their pH-activity relation under conditions which are indicated in the Figures (10-20). The pH-activity profile of a mutant is the result of the effect of the mutation on the $pK_a$ on the one hand, and the effect on the $K_{ass}$ on the other hand.

The results for the following mutants are given in the Figures:

F254K (FIG. 10), F94R (FIG. 11), F61K (FIG. 12), A25K (FIG. 13), D57N (FIG. 14), L258K (FIG. 15), Q204K (FIG. 16), R23Q (FIG. 17), H54N (FIG. 18), H290N (FIG. 19), T95D (FIG. 20.).

For the mutants in which a positive charge (F254K, F94R, F61K, A25K, L258K, Q204K) was introduced or a negative charge neutralized (D57N), it can be seen that the acidic-side of the pH-activity profile is shifted towards lower pH.

For mutants in which a negative charge was introduced (T95D) or a positive charge was neutralized (R23Q, H54N, H290N, it can be seen that the pH-activity profile is shifted towards higher pH.

Both of these observations are in agreement with the model as presented in the detailed description of the invention.

However, it should be noted that mutants in which a conserved amino acid has been replaced (F94R, D57N, H54N) give a drastic decrease in specific activity on xylose. At position 254 in the sequence alignment (FIG. 2) only hydrophobic amino acids are found. Introduction of a charged amino acid (F254K) at this position also leads to a drastic decrease in specific activity. Thus, it can be concluded that although (semi)conserved amino acid positions can be used to alter charges in order to modify the pH-activity profile they are not preferred sites.

EXAMPLE 7

Stabilization of mutants with an altered pH optimum to obtain better performance under application conditions The mutants H290N and F61K give the expected shift in the pH-activity profile as described in Example 6. Of these mutants H290N was immobilized as described in EP-A-351029 (Example 7). Application testing of the wildtype and this mutant glucose isomerase was performed as described in the same application (Example 8). The stability is indicated by the first order decay constant ($K_d$, the lower the decay constant the more stable the enzyme). Table 2 gives the $K_d$ values for the wild-type and mutant glucose isomerases.

TABLE 2

| Decay constants for wildtype and mutant glucose isomerase, immobilized on Lewatit | |
|---|---|
| | $K_d$ ($\times$ 10$^6$ sec$^{-1}$) |
| Wildtype | 2.5 |
| H290N | 3.1 |
| K253R | 0.7 |
| H290NK253R | 1.6 |
| F61KK253R | 1.4 |

As can be seen in Table 2, H290N is destabilized as compared with the wildtype glucose isomerase. K253R was found to stabilize the wildtype glucose isomerase by a factor larger than three. The pH-activity profile of the K253R mutant is identical with that of the wildtype enzyme. The combination of the pH mutant H290N with the stability mutant K253R shows that pH mutants can be stabilized by introducing mutations that have been shown to stabilize the wildtype enzyme.

In addition Table 2 shows that pH mutant F61K is stabilized with respect to the wiltype enzyme after introduction of K253R.

The acidic shift of the pH-activity profile of F61K is maintained in the double mutant (FIG. 21). This shows that mutations which improve different properties of an enzyme can be combined in a new mutant which harbours the improved properties of the individual mutations (an improved pH optimum and an improved stability in this case).

It is to be understood that the above mentioned examples are meant to demonstrate the concept of the invention and that they are not meant to limit the scope. In view of this it should be clear that combinations of the above mentioned mutations with other mutations leading to altered characteristics, e.g. thermostability, metal binding or substrate specificity, are also encompassed by the subject invention.

We claim:

1. A substantially pure, recombinantly produced, modified procaryotic glucose isomerase containing a modification wherein at least one and no more than four amino acid residues from the corresponding naturally occurring glucose isomerase within a sphere of 15 Å of a bivalent metal cation coordination site is replaced by a more negatively charged amino acid, which modified glucose isomerase exhibits an altered pH/activity profile wherein at least the acidic part of the pH/activity profile is shifted to a higher pH value and wherein said modified glucose isomerase retains glucose isomerase activity.

2. The modified glucose isomerase of claim 1 wherein the corresponding naturally-occurring glucose isomerase is derived from a microorganism of the order Actinomycetales.

3. The modified glucose isomerase of claim 2 wherein the Actinomycetales microorganism is *Actinoplanes missouriensis*.

4. The modified glucose isomerase of claim 1 wherein said at least one amino acid of the corresponding naturally-occurring glucose isomerase replaced is selected from the group consisting of:

Ala5, Phe11, Leu15, Trp20, Gln21, Arg23, Ala25, Phe26, Asp28, Ala29, Gly47, Tyr49, Thr52, Phe53, His54, Asp56, Asp57, Phe61, Ile85, Met88, Phe94, Thr95, Phe104, Gln122, Thr133, Leu134, Val135, Ala143, Tyr145, Tyr158, Asn163, Ser169, Glu181, Asn185, Glu186, Gly189, Ile191, Pro194, His198, Gln204, Leu211, Phe212, Asn215, Glu217, Thr218,

His220, Glu221, Gln222, Ser224, Asn225, Leu226, Phe228, Thr229, Gly231, Leu236, His238, His243, Asp245, Asn247, His250, Phe254, Asp255, Gln256, Asp275, Leu258, Val259, Phe260, His262, Leu271, Tyr285, Asp286, His290, Asp292, Tyr293, Lys294, Thr298, Glu299, Trp305, Ala310, Met314, Val380, and Asn383, said positions referring to the wildtype glucose isomerase of *Actinopolanes missouriensis*, and wherein said amino acid replaced is an amino acid of the wildtype glucose isomerase of *Actinoplanes missouriensis* or is an amino acid at a corresponding position in a homologous glucose isomerase.

5. The modified glucose isomerase of claim 4 wherein said replaced amino acid is selected from the group consisting of:

Ala5, Leu15, Gln21, Arg23, Ala25, Phe26, Asp28, Ala29, Gly47, Tyr49, Thr52, Asp56, Phe61, Ile85, Met88, Thr95, Phe104, Gln122, Thr133, Leu134, Ala143, Tyr145, Tyr158, Asn163, Ser169, Asn185, Gly189, Ile191, Pro194, His198, Gln204, Leu211, Phe212, Thr218, Gln222, Ser224, Asn225, Leu226, Phe228, Thr229, Gly231, Leu236, His238, His243, His250, Phe254, Gln256, Asp257, Leu258, Val259, His262, Leu271, Tyr285, Asp286, His290, Tyr293, Lys294, Thr298, Glu299, Trp305, Ala310, Met314, Val380, and Asn383, said positions referring to the wildtype glucose isomerase of *Actinopolanes missouriensis*, and wherein said amino acid replaced is an amino acid of the wildtype glucose isomerase of *Actinoplanes missouriensis* or is an amino acid at a corresponding position in a homologous glucose isomerase.

6. The modified glucose isomerase of claim 5 wherein said replaced amino acid residue is selected from the group consisting of:

Ala25, Arg23, Gly47, Tyr49, Thr52, Phe61, Ile85, Thr95, Gln122, Thr133, Tyr145, Tyr158, Gly189, Ile191, Gln204, Thr218, Gln222, Leu226, Thr229, Gly231, Leu236, Gln256, Leu258, Try293, Lys294 and Val380, said positions referring to the wildtype glucose isomerase of *Actinopolanes missouriensis*, and wherein said amino acid replaced is an amino acid of the wildtype glucose isomerase of *Actinoplanes missouriensis* or is an amino acid at a corresponding position in a homologous glucose isomerase.

7. The modified glucose isomerase of claim 6 wherein said amino acid replacement is selected from the group consisting of:

R23Q, H54N, T95D, H290N, and K294Q said positions referring to the wild-type glucose isomerase of *Actinoplanes missouriensis*, or wherein said amino acid replaced is an amino acid at a corresponding position in a homologous glucose isomerase.

8. The modified glucose isomerase of claim 7 wherein said amino acid replacement is R23Q.

9. The modified glucose isomerase of claim 7 wherein said amino acid replacement is H54N.

10. The modified glucose isomerase of claim 7 wherein said amino acid replacement is T95D.

11. The modified glucose isomerase of claim 7 wherein said amino acid replacement is H290N.

12. The modified glucose isomerase of claim 7 wherein said amino acid replacement is K294Q.

13. A method to produce a modified glucose isomerase of claim 1, which process comprises:

mutating a DNA sequence encoding a wildtype glucose isomerase at selected nucleotide positions;

cloning the mutated sequence into an expression vector in such a manner that the DNA sequence can be expressed;

transforming a host organism or cell with the vector;

culturing the host organism or cell; and isolating the modified glucose isomerase from the culture.

14. A process for producing the modified glucose isomerase of claim 1 which comprises culturing a host organism transformed with a mutated glucose isomerase DNA cloned into an expression vector in such a manner that the DNA sequence can be expressed under conditions which favor expression and isolating the modified glucose isomerase from the culture.

15. A method for altering the pH specificity of a procaryotic glucose isomerase wherein at least the acidic part of the pH/activity profile is shifted to a higher pH value and wherein said modified glucose isomerase retains glucose isomerase activity a more negatively charged amino acid which method comprises substituting for at least one and no more than four amino acid residues from the corresponding naturally occurring glucose isomerase within a sphere of 15 Å of a bivalent metal cation coordination site.

* * * * *